US011278353B2

(12) United States Patent
Sela et al.

(10) Patent No.: US 11,278,353 B2
(45) Date of Patent: Mar. 22, 2022

(54) TRAJECTORY ALIGNMENT SYSTEM AND METHODS

(71) Applicant: SYNAPTIVE MEDICAL INC., Toronto (CA)

(72) Inventors: Gal Sela, Toronto (CA); Neil Jeffrey Witcomb, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 1552 days.

(21) Appl. No.: 15/071,251

(22) Filed: Mar. 16, 2016

(65) Prior Publication Data
US 2017/0265943 A1 Sep. 21, 2017

(51) Int. Cl.
*A61B 34/10* (2016.01)
*G16H 40/63* (2018.01)
(Continued)

(52) U.S. Cl.
CPC .............. *A61B 34/10* (2016.02); *A61B 34/20* (2016.02); *G16H 40/63* (2018.01); *G16Z 99/00* (2019.02); *A61B 17/34* (2013.01); *A61B 34/25* (2016.02); *A61B 2034/107* (2016.02); *A61B 2034/2051* (2016.02); *A61B 2034/2055* (2016.02);
(Continued)

(58) Field of Classification Search
CPC . A61B 34/20; A61B 34/10; A61B 2034/2051; A61B 2034/2068; A61B 17/34; A61B 2034/2055; A61B 2090/3983; A61B 2034/107; A61B 34/25; G16H 40/63; G06F 19/00
See application file for complete search history.

(56) References Cited

U.S. PATENT DOCUMENTS 8,116,848 B2  2/2012  Shahidi
2006/0094953 A1  5/2006  Hartlep et al.
(Continued)

FOREIGN PATENT DOCUMENTS

WO    WO0056215 A1   9/2000
WO       0176497 A1  10/2001
(Continued)

OTHER PUBLICATIONS

NPO, Combined Search and Examination Report relating to NL application No. NL2018529, dated Mar. 16, 2017.
(Continued)

*Primary Examiner* — Rochelle D Turchen

(57) ABSTRACT

The navigation systems and methods facilitate aligning a tool in relation to a trajectory in real-time to receive input data from a pre-operative plan image, at least one multi-modal image, and at least one real-time multi-modal image; interactively track at least one neural fiber, whereby interactively tracked fiber data is obtainable; automatically generate output data by way of data transformation using the input data and the interactively tracked neural fiber data; and transmit the output data to at least one of: at least one display device for rendering at least one real-time interactive navigation display for facilitating neural navigation, and at least one drive device for positioning at least one tracking device in relation to the tool in real-time, whereby real-time alignment data is achievable, and whereby at least one neurological structure is preservable.

10 Claims, 25 Drawing Sheets

(51) Int. Cl.
   *A61B 34/20* (2016.01)
   *G16Z 99/00* (2019.01)
   *A61B 17/34* (2006.01)
   *A61B 90/00* (2016.01)
   *A61B 34/00* (2016.01)

(52) U.S. Cl.
   CPC ............. *A61B 2034/2068* (2016.02); *A61B 2090/3983* (2016.02)

(56) References Cited

U.S. PATENT DOCUMENTS

| | | |
|---|---|---|
| 2008/0300477 A1 | 12/2008 | Lloyd et al. |
| 2010/0081914 A1 | 4/2010 | Waynik et al. |
| 2012/0184844 A1 | 7/2012 | Gielen et al. |
| 2013/0085344 A1 | 4/2013 | Merkl et al. |
| 2014/0135791 A1* | 5/2014 | Nikou .................. A61B 34/30 606/130 |
| 2015/0227702 A1* | 8/2015 | Krishna ............... A61B 5/4094 705/2 |
| 2016/0022171 A1 | 1/2016 | Lin et al. |
| 2016/0256069 A1* | 9/2016 | Jenkins ............... A61B 5/0042 |

FOREIGN PATENT DOCUMENTS

| | | | |
|---|---|---|---|
| WO | 2014138916 A1 | 9/2014 | |
| WO | 2014139019 A1 | 9/2014 | |
| WO | 2014139021 A1 | 9/2014 | |
| WO | 2014139022 A1 | 9/2014 | |
| WO | 2014139024 A1 | 9/2014 | |
| WO | WO2014139021 A1 | 9/2014 | |
| WO | WO-2014139022 A1 * | 9/2014 | ............ A61B 5/065 |
| WO | WO2015135055 A1 | 9/2015 | |
| WO | WO2015135057 A1 | 9/2015 | |
| WO | WO2016026021 A1 | 2/2016 | |

OTHER PUBLICATIONS

UKIPO, Combined Search and Examination Report relating to GB application No. GB1704050.2, dated Nov. 14, 2017.

* cited by examiner

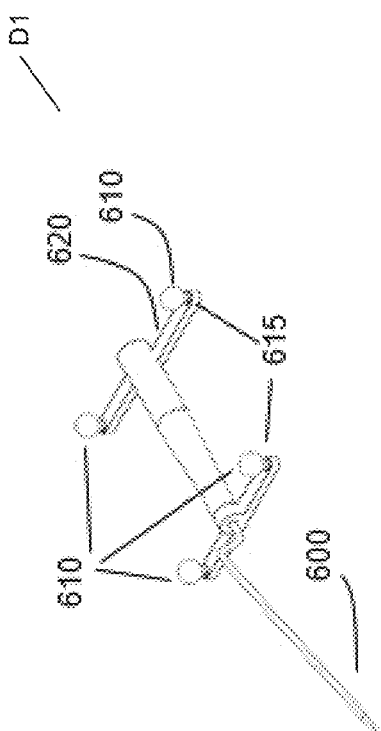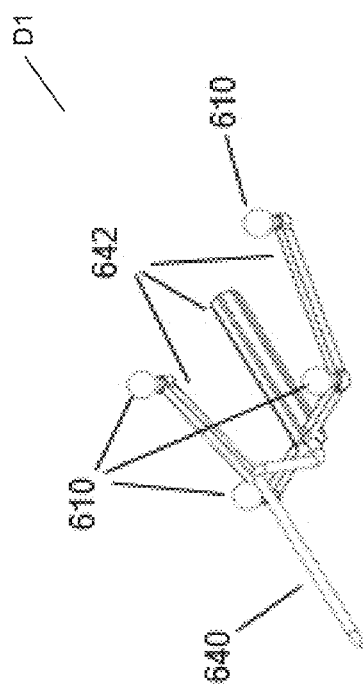
FIG. 6A
FIG. 6B

TRAJECTORY ALIGNMENT SYSTEM AND METHODS

TECHNICAL FIELD

The subject matter of the present disclosure generally relates to the field of image guided medical procedures.

More particularly, the subject matter of the present disclosure technically relates to the field of patient reference tools for rapid registration in relation to image guided medical procedures. Even more particularly, the subject matter of the present disclosure technically relates to the field of assisting patient reference tools for rapid registration in relation to image guided medical procedures.

BACKGROUND

In the related art, surgery, such as neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, radiofrequency, or optical tracking devices. As a set, these devices are commonly referred to as surgical navigation systems and are often cumbersome and provide inaccurate tracking.

Port-based surgery is a minimally invasive surgical technique where a port is introduced to access a surgical region of interest using surgical tools. Unlike other minimally invasive techniques, such as laparoscopic techniques, a port diameter is larger than a tool diameter. Hence, the tissue region of interest is visible through the port, wherein exposed tissue in a region of interest, at a depth few centimetres below the skin surface, is accessible through a narrow corridor in the port.

Several related art problems generally preclude or impair the ability to perform port-based navigation in an intraoperative setting. For example, the position of the port axis relative to a typical tracking device (TD) is a free and uncontrolled parameter that prohibits the determination of access port orientation. Further, the limited access which is available, due to the required equipment for the procedure, causes indirect access port tracking to be impractical and unfeasible. Also, the requirement for angulation of the access port to access many areas within the brain during a procedure makes navigation of the access port a difficult and challenging problem that has not yet been addressed.

Further, a recent paper by Stieglitz et al., "The Silent Loss of Neuronavigation Accuracy: A Systematic Retrospective Analysis of Factors Influencing the Mismatch of Frameless Stereotactic Systems in Cranial Neurosurgery," highlights the need for accurate navigation, wherein after patient registration, an ongoing loss of neuro-navigation accuracy remains due to other mitigating factors related to the surgical procedure, i.e., draping, attachment of skin retractors, and duration of surgery. Surgeons should be aware of this "silent" loss of accuracy when using related art navigation systems.

Accordingly, challenges experienced in the related art include an inability to perform a real-time registration of a surgical trajectory in relation to the unique characteristics of a particular tissue types or sub-types, such as in relation to cerebral tissue. Therefore, a need exists for a system and method that integrates and updates pre-operative and intraoperative plans into navigation systems for minimally invasive surgical procedures, such as an improved system and method for mapping navigation space to patient space in a medical procedure, e.g., as a real-time registration of a surgical trajectory in relation to the unique characteristics of a particular tissue types or sub-types, for example, cerebral tissue.

BRIEF SUMMARY

The present disclosure addresses at least many of the foregoing challenges experienced by related art registration devices and methods, by way of a system and methods for aligning a trajectory, such as a therapeutic trajectory, a medical trajectory, and/or a surgical trajectory, in real-time, whereby axonal connections, neural fibers, and neural pathways are preservable, and whereby damage to brain circuitry is preventable. The presently disclosed system and methods for aligning a surgical trajectory in real-time involve registration by way of multi-modal imaging for providing transformed real-time data to a user interface, the transformed data comprising real-time registration data in relation to real-time neural network data, such real-time registration data renderable by way of user interface, e.g., a display device. The present disclosure applies equally well to catheters, DBS needles, a biopsy procedure, and also to biopsies and/or catheters in other medical procedures performed on other parts of the body. To date, such capabilities have been hitherto unknown in the related art.

In accordance with an embodiment of the present disclosure, a medical navigation system and methods are used to execute a surgical plan during brain medical procedures. These procedures may include port-based surgery using a port with an introducer, deep brain stimulation, or brain biopsy using needles. The navigation system, comprising navigation software module, is configured to utilize a medical plan or a surgical plan ("plan") based on a multi-segment path trajectory, previously prepared or predetermined using pre-operative anatomical information of a given patient's brain. This plan is imported into the navigation software module.

Prior to commencing the procedure, the brain is registered using the corresponding pre-operative anatomical information, in accordance with an embodiment of the present disclosure. Once the craniotomy has been performed, the navigation system and methods utilize a user interface for displaying an overlay image of the brain and the multipoint path trajectory. In addition, the user interface provides a guidance mechanism to assist the surgeon in aligning the surgical tool, such as a port, a biopsy needle, a catheter, and the like, e.g., coaxially along a first path trajectory segment. Using port-based surgery as an example, once the port is aligned with the first path trajectory segment, the surgeon begins a cannulation procedure and moves the port introducer along the first path trajectory segment while the system and method assist the surgeon in remaining consistently coaxial in relation to the first path trajectory segment, the user interface displaying, to the surgeon, the distance of the introducer along the first path trajectory segment until the end of the first path trajectory segment is reached. The surgeon then changes direction to follow a second path trajectory segment. The process is repeated until the target location is reached.

The system and methods of the present disclosure provide the surgeon with positional information of the patient's anatomy of interest throughout the course of the medical procedure using video overlay, e.g., allowing the surgeon to see the brain through the drapes and, therefore, know his/her orientation relative to the patient. By so doing, the surgeon more accurately identifies potential locations of anatomical structures of the brain intra-operatively, as opposed to performing the procedure without a rendered overlay of the anatomical part as otherwise practiced in the related art. The system and methods allow facilitates confirmation that the correct anatomical data of the patient more effectively than presently used systems for at least that the imaged anatomy is rendered onto the real-time imaging of the patient anatomy, thereby allowing the surgeon to compare the rendered image of the anatomical part with the real anatomical part, for example, comparing the sulci locations during a port procedure.

The system and methods of the present disclosure provide tracking of multiple tools relative to the brain during surgery so that the surgeon is not "flying blind." For example the system can track the port as well as any tool being used in conjunction with the port, such as a resection tool in the case of tumor resection, whereas related art systems track only a pointer tool. The navigation system and methods provide the surgical team with a setup for the surgery based on a predetermined plan, e.g., a setup of the head clamp, position of patient, tracking device, etc., to prevent readjustments of such elements during surgery. The navigation system and methods adaptively update a section of a larger pre-operative MRI image by using a localized intra-operative MRI image (given that the brain is internally accessible from within the skull). The navigation system and methods may provide positionally accurate maps (images) correlating intra-operative information acquired during surgery, such as hyperspectral and Raman signatures, to locations at which the information is acquired. For example, these Raman signatures may be represented by spatially correlated color maps.

The system and methods of the present disclosure, while primarily described for port-based brain surgery, is not limited to port based brain surgery, but is also applicable to any surgical or medical procedure that utilizes a navigation system. Thus, a port may not be necessary; and the anatomical part may be any part of the anatomy. This system can be utilized with any animal, including humans.

In accordance with an embodiment of the present disclosure, a system for aligning a tool in relation to a trajectory in real-time comprises: a processor configurable by a set of executable instructions storable in relation to a non-transitory memory device to: receive input data from at least one source of at least one pre-operative plan image, at least one multi-modal image, and at least one real-time multi-modal image; interactively track at least one neural fiber, whereby interactively tracked fiber data is obtainable; automatically generate output data by way of data transformation using the input data and the interactively tracked neural fiber data; and transmit the output data to at least one of: at least one display device for rendering at least one real-time interactive navigation display for facilitating neural navigation, and at least one drive device for positioning at least one tracking device in relation to the tool in real-time, whereby real-time alignment data is achievable, and whereby at least one neurological structure is preservable.

In accordance with another embodiment of the present disclosure, a method of fabricating a system for aligning a tool in relation to a trajectory in real-time comprises: providing a processor configurable by a set of executable instructions storable in relation to a non-transitory memory device to: receive input data from at least one source of at least one pre-operative plan image, at least one multi-modal image, and at least one real-time multi-modal image; interactively track at least one neural fiber, whereby interactively tracked fiber data is obtainable; automatically generate output data by way of data transformation using the input data and the interactively tracked neural fiber data; and transmit the output data to at least one of: at least one display device for rendering at least one real-time interactive navigation display for facilitating neural navigation, and at least one drive device for positioning at least one tracking device in relation to the tool in real-time, whereby real-time alignment data is achievable, and whereby at least one neurological structure is preservable.

In accordance with another embodiment of the present disclosure, a method of aligning a tool in relation to a trajectory in real-time by way of an alignment system comprises: providing the alignment system, the alignment system providing comprising providing a processor configurable by a set of executable instructions storable in relation to a non-transitory memory device to: receive input data from at least one source of at least one pre-operative plan image, at least one multi-modal image, and at least one real-time multi-modal image; interactively track at least one neural fiber, whereby interactively tracked fiber data is obtainable; automatically generate output data by way of data transformation using the input data and the interactively tracked neural fiber data; and transmit the output data to at least one of: at least one display device for rendering at least one real-time interactive navigation display for facilitating neural navigation, and at least one drive device for positioning at least one tracking device in relation to the tool in real-time, whereby real-time alignment data is achievable, and whereby at least one neurological structure is preservable; calibrating the tool by using a calibration block; if performing a port procedure, verifying a port; evaluating an approach by determining whether a planned engagement point is appropriate using the at least one real-time interactive navigation display of the alignment system; if the planned engagement point is appropriate, performing the approach; if the planned engagement point is inappropriate, interactively setting a new engagement point by way of at least one interactive feature of the alignment system; and optionally returning to the evaluating step.

Benefits of the system and methods of the present disclosure include, but are not limited to, eliminating the necessity of a tracked sheath for aligning a port, facilitating alignment of compatible miniframes, such as Monteris® miniframes, facilitating an approach by way of a pointer, facilitating locating an entry point by using real-time registration data renderable, such as by real-time graphics, via a user interface, e.g., on a display device, and displaying a trajectory length (or pathway) in at least one of the stage of craniotomy, approach, and resection.

Some of the features in the present disclosure are broadly outlined in order that the section entitled Detailed Description is better understood and that the present contribution to the art may be better appreciated. Additional features of the present disclosure are described hereinafter. In this respect, understood is that the present disclosure is not limited in its application to the details of the components or steps set forth herein or as illustrated in the several figures of the being carried out in various ways. Also, understood is that the phraseology and terminology employed herein are for the purpose of the description and should not be regarded as limiting.

BRIEF DESCRIPTION OF THE DRAWINGS

The above, and other, aspects, features, and advantages of several embodiments of the present disclosure will be more apparent from the following Detailed Description as presented in conjunction with the following several figures of the Drawing.

FIG. 6A is a diagram illustrating a perspective view of a patient reference device comprising a tracking tool, in accordance with an embodiment of the present disclosure.

FIG. 6B is a diagram illustrating a perspective view of a patient reference device comprising a tracking tool, in accordance with an embodiment of the present disclosure.

Figure 1:
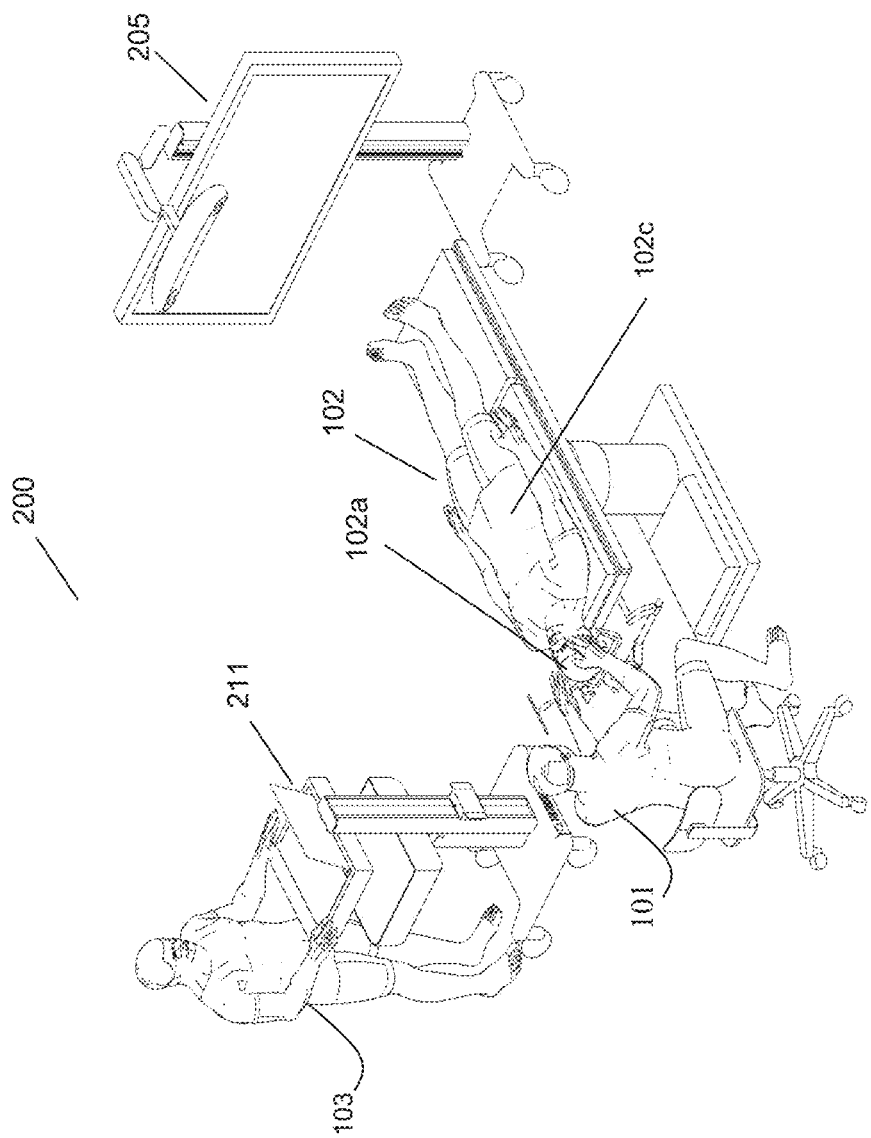
FIG. 1 is a diagram illustrating a perspective view of a navigation system, such as a medical navigation system, comprising a patent reference device, in an environmental context, such as an operation room, of in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

The systems and methods described herein are useful in the field neurosurgery, including oncological care, neurodegenerative disease, stroke, brain trauma, and orthopedic surgery. However, the subject matter of the present disclosure may extend or apply to other conditions or fields of medicine; and such extensions or applications are encompassed by the present disclosure. The systems and methods described herein encompass surgical processes that are applicable to surgical procedures for brain, spine, knee, and any other region of the body that will benefit from the use of an access port or small orifice to access the interior of an animal body, such as a human body.

Various systems, apparatuses, devices, or processes are below-described and provide examples of the navigation systems and methods embodiments, in accordance with embodiments of the present disclosure. None of the below-described embodiments limits any claimed embodiment; and any claimed embodiment may also encompass systems, apparatuses, devices, or processes which may differ from below-described examples. The claimed embodiments are not limited to systems, apparatuses, devices, or processes having all of the features of any one of the below-described systems, apparatuses, devices, or processes or to features common to some or all of the below-described systems, apparatuses, devices, or processes.

Furthermore, this Detailed Description sets forth numerous specific details in order to provide a thorough understanding of the various embodiments described throughout the present disclosure. However, it will be understood by those of ordinary skill in the art that the embodiments described herein may be practiced without these specific details. In other instances, well-known methods, procedures and components have not been described in detail so as not to obscure the embodiments described herein.

Figure 2:
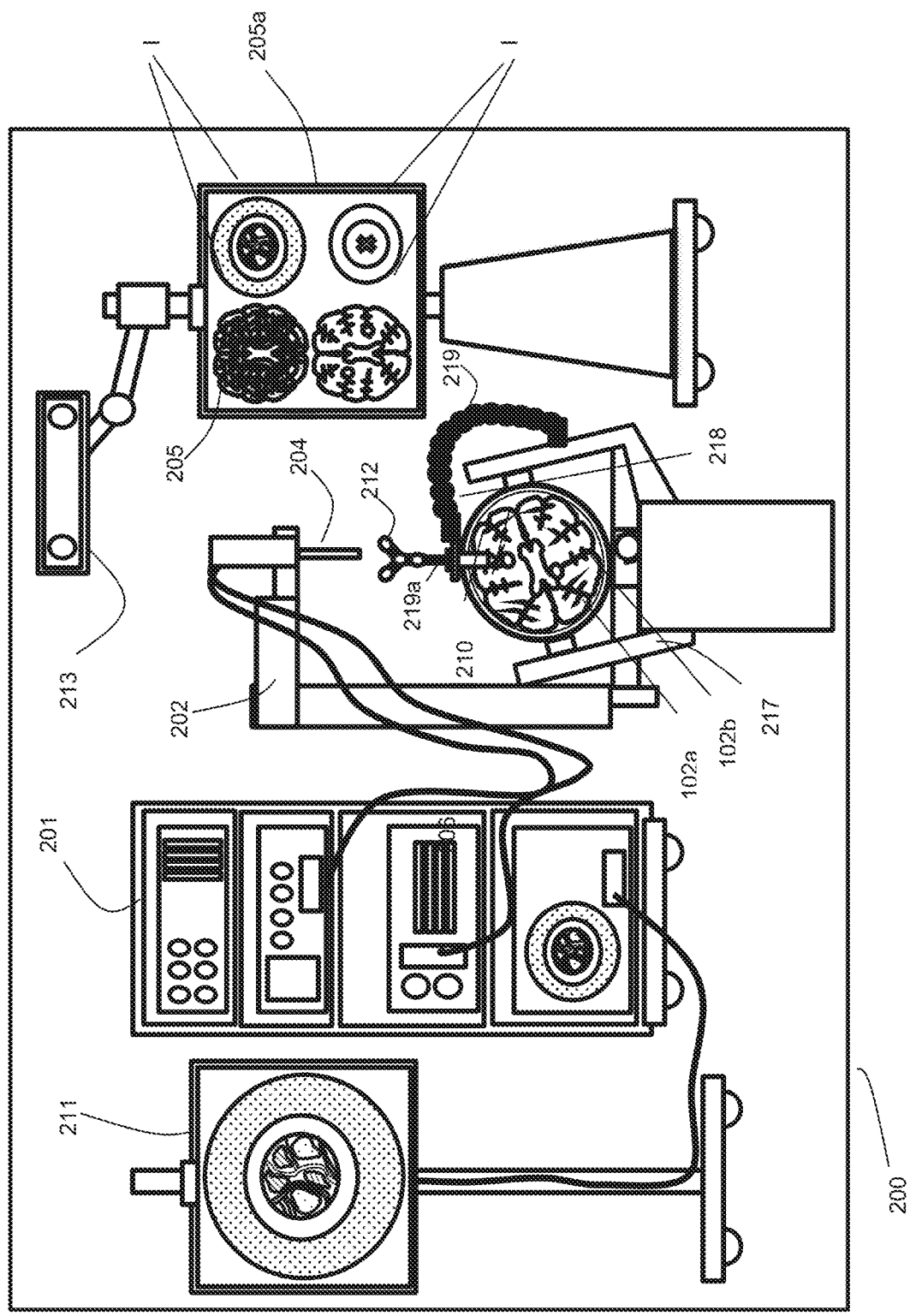
FIG. 2 is a schematic diagram illustrating a navigation system, such as a medical navigation system, comprising a patent reference device, in accordance with an embodiment of the present disclosure.

Referring to FIG. 1, this diagram illustrates, in a perspective view, a navigation system 200, such as a medical navigation system, comprising a patent reference device, in an environmental context, such as an operation room (OR), of in accordance with an embodiment of the present disclosure. The system 200 supports, facilitates, and enhances minimally invasive access port based surgery using a minimally invasive access port based surgical procedure. By example only, a surgeon 101 conducts a minimally invasive access port based surgery on a subject, such as a patient 102, in an OR environment. The navigation system 200, comprising an equipment tower 201, a tracking system 213, at least one display device, e.g., a primary display device 211 and a secondary display device 205, the system 200 configured to track at least one instrument, such as a surgical instrument, e.g., an access port 206 and an introducer 210, and/or a tool, such as a tracking tool, e.g., a pointer, for assisting the surgeon 101 during the minimally invasive access port based surgical procedure (FIG. 2). By example only, an operator 103 is also present to operate, control, and provide assistance for the system 200.

Referring to FIG. 2, this schematic diagram illustrates a medical navigation system, comprising an equipment tower 201, a tracking system 213, at least one display device. e.g., a primary display device 211 and a secondary display device 205, the system 200 configured to track at least one instrument, such as a surgical instrument, e.g., an access port 206 and an introducer 210, and/or a tool, such as a tracking tool, e.g., a pointer, for assisting the surgeon 101 during the minimally invasive access port based surgical procedure, in accordance with an embodiment of the present disclosure. By example only, the navigation system 200 comprises a display device 211, such as a monitor, for displaying a video image, an equipment tower 201 for accommodating at least one piece of equipment, a robotic arm 202, an optical scope 204 coupled with at least one piece of equipment and supportable by the robotic arm 202.

Still referring to FIG. 2, the equipment tower 201 is mountable on a frame, e.g., a rack or a cart, and is configured to accommodate at least one of a computer operable by at least one a set of instructions, storable in relation to at least one non-transitory memory device, corresponding to at least one of planning software, navigation software, and robotic software for managing at least one of the robotic arm 202 and the at least one instrument, such as a surgical instrument, e.g., an access port 206 and an introducer 210, and/or a tool, such as a tracking tool, e.g., a pointer, and a power supply, e.g., an AC adapter power supply. The computer comprises at least one of a control unit and a processing unit, e.g., a control and processing unit 400 (FIG. 8), for example. The equipment tower 201 comprises a single tower configured to facilitate coupling of the at least one display device. e.g., a primary display device 211 and a secondary display device 205, with the at least one piece of equipment. However, other configurations are also encompassed by the present disclosure, such as the equipment tower 201 comprising dual towers configured to facilitate coupling of a single display, etc. Also, the equipment tower 201 is also configurable to accommodate an uninterruptible power supply (UPS) for providing emergency power.

Still referring to FIG. 2, a patient's head is retained by a head holder 217, a craniotomy is performed, a dura flap is formed and retracted, and the access port 206 and the introducer 210 are inserted into the patient's brain 102a. The introducer 210 further comprises a pointing tool. The introducer 210 is trackable by way of the tracking system 213, whereby position information is used in the navigation system 200. The tracking system 213 is configured to track and determine, e.g., in real-time by way of a set of instructions corresponding to tracking software and storable in relation to at least one non-transitory memory device, location data of at least one OR item, such as the robotic arm 202 and the at least one instrument, such as a surgical instrument, e.g., an access port 206 and an introducer 210, and/or a tool, such as a tracking tool, e.g., a pointer. The tracking system 213 comprises at least one sensor (not shown) for detecting at least one fiducial marker 212 disposable in relation to the at least one OR item, e.g., the robotic arm 202 and the at least one instrument, such as a surgical instrument, e.g., an access port 206 and an introducer 210, and/or a tool, such as a tracking tool, e.g., a pointer. The tracking system 213 comprises a three-dimensional (3D) optical tracking stereo camera, such as a Northern Digital Imaging® (NDI) optical tracking stereo camera, by example only. The secondary display device 205 is configured to display real-time output 205a from the tracking system 213. The output 205a comprises a display of at least one of an axial view, a sagittal view, at least one coronal view, and a view oriented relative to the at least one instrument, such as perpendicular to a tool tip, in-plane of a tool shaft, etc. The output 205a further comprises a display of multiple views.

Still referring to FIG. 2, minimally invasive brain surgery using access ports is a recent method of performing surgery on brain tumors. In order to introduce an access port 206 into a brain, such as the patient brain 102b, of a patient head 102a, an introducer, e.g., the introducer 210, comprises an atraumatic tip disposable within the access port 206 for facilitating positioning the access port 206 within the patient brain 102a. The introducer 210 further comprises at least one fiducial marker 212 for facilitating tracking by the tracking system 213. The at least one fiducial marker 212 comprises at least one of at least one reflective sphere (not shown) for use with a tracking system 213 comprising an optical tracking stereo camera (not shown) and at least one pick-up coil (not shown) for use with a tracking system 213 comprising an electromagnetic tracking device (not shown). The at least one fiducial marker 212 is detectable by the at least one sensor (not shown) of the tracking system 213; and the position of the at least one fiducial marker 212 is determined by the tracking system 213 operating by way of the tracking software. In a preferred embodiment of the present disclosure, the at least one fiducial marker 212 comprises a plurality of fiducial markers 212.

Still referring to FIG. 2, after the introducer 210 and the access port 206 are inserted into the brain 102b, the introducer 210 is removed to facilitate access to tissue of the brain 102b through a central opening of the access port 206. However, after the introducer 210 is removed, the access port 206 is no longer being trackable by the tracking system 213. Accordingly, the access port 206 is indirectly trackable by way of additional pointing tools (not shown) configured for identification by the navigation system 200.

Still referring to FIG. 2, the navigation system 200 further comprises a guide clamp 218 for retaining the access port 206. The guide clamp 218 is configured to optionally engage and disengage the access port 206, eliminating the need to remove the access port 206 from the patient 102. In some embodiments, the access port 206 is configured to slide up and down within the guide clamp 218 in a closed position. The guide clamp 218 further comprises a locking mechanism (not shown), the locking mechanism being attachable or integrable in relation to the guide clamp 218, and the locking mechanism being optionally manually actuable, e.g., using one hand as further below described.

Still referring to FIG. 2, the navigation system 200 further comprises an articulating arm 219, such as a small articulating arm, configured to couple with the guide clamp 218. The articulating arm 219 comprises up to six (6) degrees of freedom for facilitating positioning of the guide clamp 218. The articulating arm 219 is attachable at a location in relation to the head holder 217, or in relation to any other suitable patient support structure, to ensure, when locked in place, that the guide clamp 218 is fixed in relation to the patient's head 102a. The articulating arm 219 comprises an interface 219a disposable in relation to the guide clamp 218, wherein the interface 219a is at least one of flexible and lockable into place. Flexibility of the interface 219a facilitates movability of the access port 206 into various positions within the brain 102b, yet still maintains rotability about a fixed point.

Still referring to FIG. 2, by example only, the interface 219a comprises a linkage, such as a slender bar or a slender rod. When the access port 206 is moved to various positions, the interface 219a is configured to oppose a bending force, whereby the access port 206 is returnable to a centered position. The interface 219a further comprises an optional collar engageable with the linkage between the articulating arm 219, and the guide clamp 218, such that, when engaged, the linkage becomes rigid. Currently, no such mechanisms are known to exist in the related art to enable positioning an access port 206 in such manner.

Still referring to FIG. 2, the navigation system 200, comprising preset equipment and components, further facilitates setup of a surgical procedure which may be otherwise complex and lengthy in the related art for at least the reason that many pieces of equipment associated with a surgical procedure must be coordinated. In an alternative embodiment of the present disclosure, navigation system 200 provides a solution to the related art problems, and comprises a plurality of wide-field cameras, e.g., two additional wide-field cameras (not shown) being implemented with video overlay information, wherein one camera, e.g., a first additional camera, of the two additional wide-field cameras is mountable in relation to the optical scope 204; and the other camera, e.g., a second additional camera, of the two additional wide-field cameras is mountable in relation to the navigation system 213. Alternatively, in the case of the navigation system 213 comprising an optical tracking device, a video image is directly extractable from the second additional camera of the tracking system 213. Video overlay information is then insertable into the images, wherein the video overlay provides at least one of type of information, such an image displaying a physical space and confirm tracking system registration alignment and optional corresponding text and/or indicia, an image displaying a motion range of the robotic arm 202 holding the optical scope 204 and optional corresponding text and/or indicia, and an image displaying a guide head positioning and a patient positioning and optional corresponding text and/or indicia.

Figure 3A:
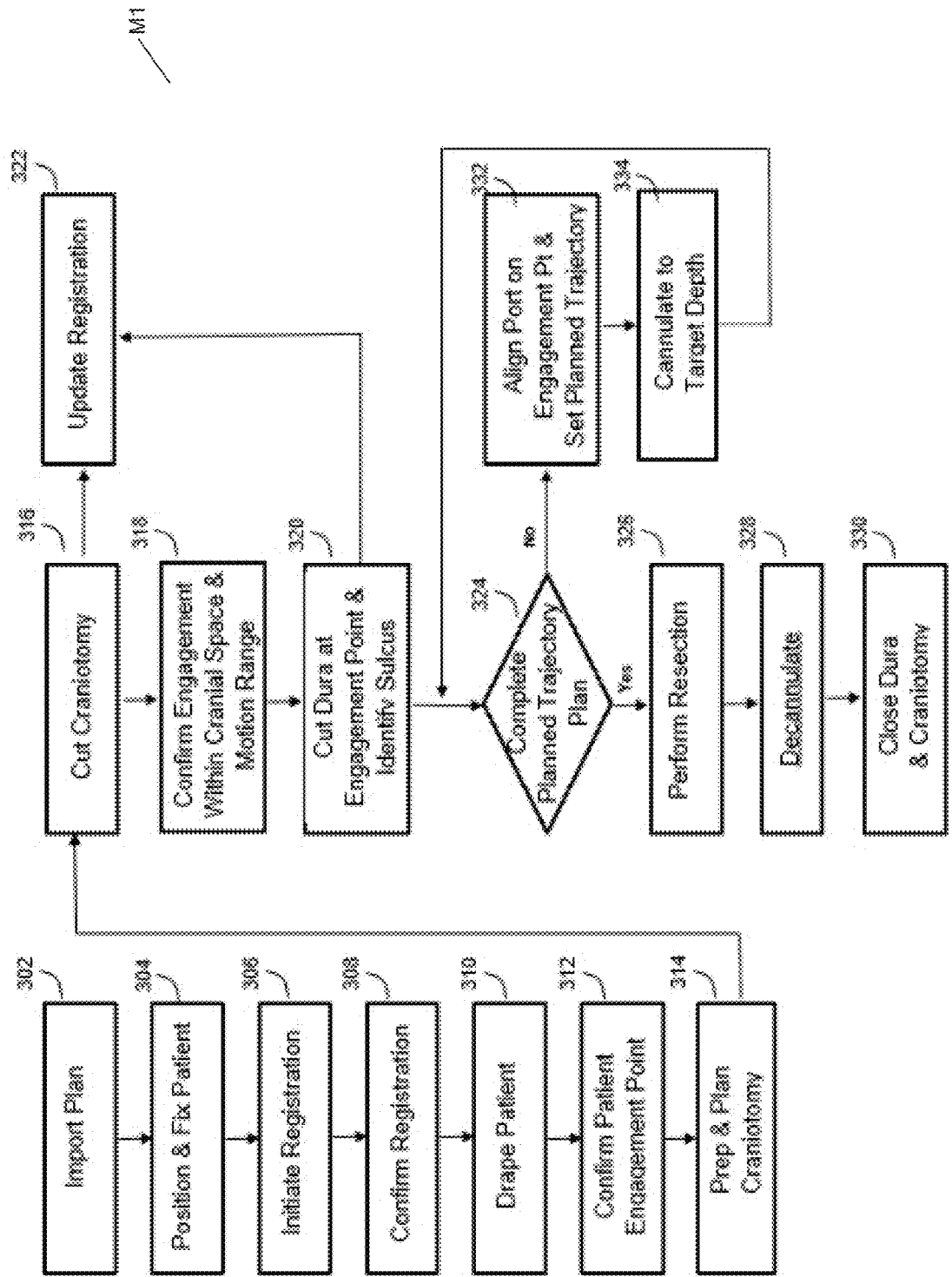
FIG. 3A is a flow diagram illustrating a method of performing a medical procedure, such as a surgical procedure, e.g., a brain biopsy using an access port, by way of a navigation system, in accordance with an embodiment of the present disclosure.

Referring to FIG. 3A, this flow diagram illustrates a method M1 of performing a medical procedure, such as a surgical procedure, e.g., a brain biopsy using an access port 206, by way of a navigation system 200, in accordance with an embodiment of the present disclosure. The method M1 comprises: importing a surgical plan, e.g., a port-based surgical plan, as indicated by block 302; positioning and fixing a patient, as indicated by block 304; initiating a registration, as indicated by block 306; confirming registration, as indicated by block 308; draping the patient, as indicated by block 310; confirming a patient engagement point, as indicated by block 312; preparing and planning a craniotomy, as indicated by block 314; cutting (e.g., incising) a cranium, as indicated by block 316; updating registration, as indicated by block 322, and confirming engagement and motion range within a cranial space, as indicated by block 318; cutting a dura at the engagement point and identifying a sulcus, as indicated by block 320; updating registration, as indicated by block 322, and determining whether a planned trajectory plan is complete, as indicated by block 324; if the planned trajectory plan is complete, performing a resection, as indicated by block 326, decannulating, as indicated by block 327, and closing the dura and closing the cranium, as indicated by block 330; or, if the planned trajectory plan is incomplete, aligning the access port 206 at the engagement point and setting the planned trajectory, as indicated by block 332, cannulating to a target depth, as indicated by block 334, and determining whether a planned trajectory is complete, as indicated by block 324.

Still referring to FIG. 3A, by example only, the method M1 further comprises: using pre-operative 3D imaging data, such as MRI data, CT scan data, ultrasound data etc.; overlaying imaging data (real-time), from received input data (interactively measured data), such as data relating to sulci entry points, target locations, surgical outcome criteria, and additional 3D image data information, on the pre-operative 3D imaging data; and displaying at least one trajectory path based on a calculated score corresponding to a projected surgical path, as described by the present disclosure and by the disclosure(s) of the priority document(s). At least one of the pre-operative 3D imaging data and the interactively measured data comprise three (3) spatial dimensions of the data set. In another embodiment of the present disclosure, the relevant parameters comprise two (2) spatial dimensions, e.g., as in the case of MR "slice" images as acquired by conventional MRI equipment) and time t being a third dimension of the data set. In another embodiment of the present disclosure, the relevant parameters comprise three (3) spatial dimensions and time t being a fourth dimension of the data set. Some imaging modalities and estimation methods, such as diffusion tensor imaging (DTI) data, may contain more than four dimensions of information at each spatial location. The method M1 may comprise executing a variety of surgical plans by way of the navigation system 200.

Still referring to FIG. 3A, the method M1 includes further detailed sub-steps. After importing a surgical plan into the navigation system 200, as indicated by block 302, positioning and fixing the patient comprises affixing the patient's head 102*a* into position using a head holder 217 and/or the patient's body 102*c* using a body holding mechanism (not shown), and confirming the head position with the patient plan using the navigation software, as indicated by block 304. In the step of initiating registration of the patient, as indicated by block 306, initiating registration, the word "registration," or the phrase "image registration" comprises transforming different sets of data into one coordinate system, whereby transformed data is provided.

Still referring to FIG. 3A, the method M1 includes yet further detailed sub-steps. For instance, registration of the patient, as indicated by block 306, can be performed in relation to a base reference frame is performable by various sub-steps, such as (a) identifying features (natural or engineered) on the MR and CT images and point to those same features in the live scene using a pointer tool that is tracked by the tracking system; (b) tracing a line on the curved profile of the patient's face or forehead with a pointer tool that is tracked by the tracking system and matching this curved profile to the 3D MR or CT volume; (c) applying a tool of known geometry to the patient's face or forehead, wherein the tool comprises at least one of an active target and a passive target, trackable by the tracking system 213; and (d) using a surface acquisition tool based on structured light and matching an extracted surface to the 3D MR or CT volume.

Still referring to FIG. 3A, those skilled in the art will appreciate that there are numerous registration techniques available and one or more of them may be used in the present application. Non-limiting examples include intensity-based methods which compare intensity patterns in images via correlation metrics, while feature-based methods find correspondence between image features such as points, lines, and contours. Image registration algorithms may also be classified according to the transformation models they use to relate the target image space to the reference image space. Another classification can be made between single-modality and multi-modality methods. Single-modality methods typically register images in the same modality acquired by the same scanner/sensor type, for example, a series of MR images can be co-registered, while multi-modality registration methods are used to register images acquired by different scanner/sensor types, for example in MRI and PET.

Still referring to FIG. 3A, in the present disclosure, the method M1 further comprises using multi-modality registration techniques from medical imaging of the head/brain obtained from different scanners e.g., from registration of brain CT/MRI images or PET/CT images for tumor localization, registration of contrast-enhanced CT images in relation to non-contrast-enhanced CT images, and registration of ultrasound and CT, and transforming such data for better interactively refining alignment of a surgical trajectory.

Figure 3B:
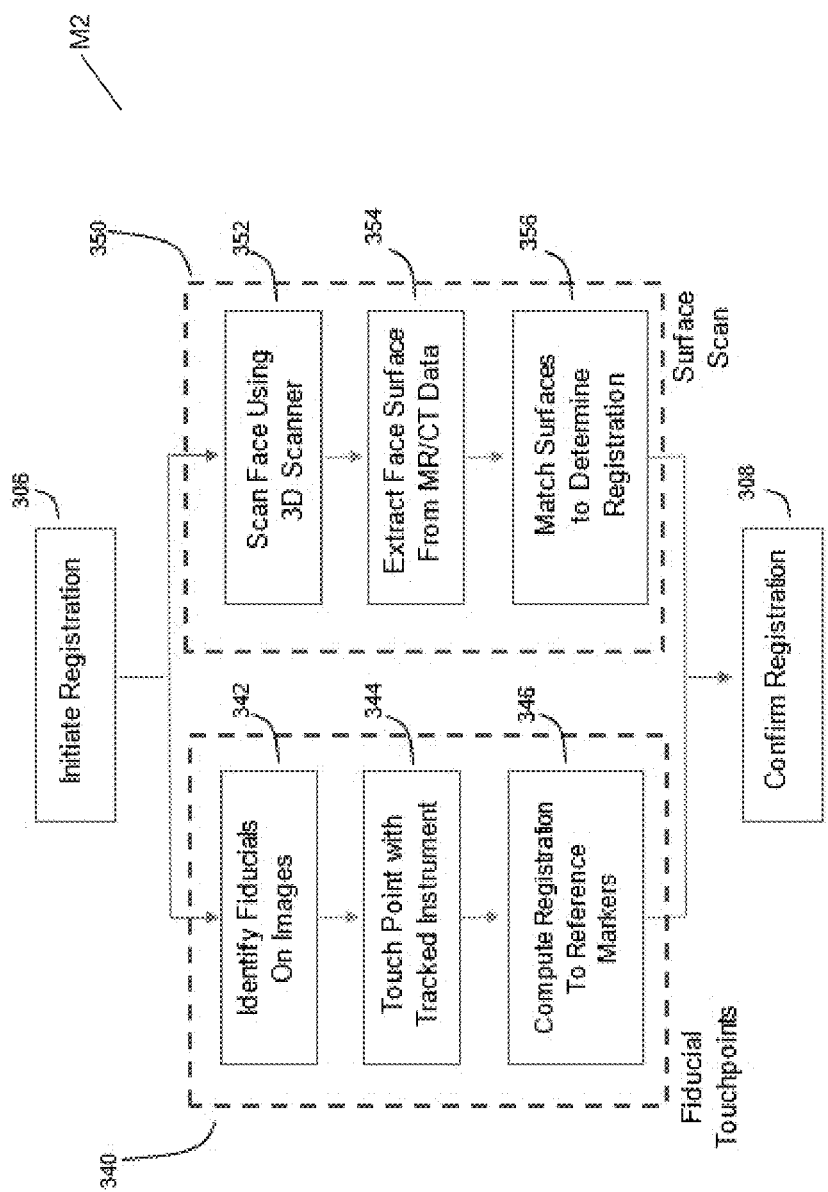
FIG. 3B is a flow diagram illustrating a partial view of a portion of the method of performing a medical procedure, such as a surgical procedure, e.g., a brain biopsy using an access port, by way of a navigation system, as shown in FIG. 3A, in accordance with an embodiment of the present disclosure.

Referring to FIG. 3B, this flow diagram illustrates, in a partial view, a portion of the method M1 of performing a medical procedure, such as a surgical procedure, e.g., a brain biopsy using an access port 206, by way of a navigation system 200, as shown in FIG. 3A, in accordance with an embodiment of the present disclosure. The method M1 further comprises: completing registration by using fiducial touch-points (FIG. 4B) captured by a pointing tool as indicated by block 340 (FIGS. 6A-6D), wherein completing registration by using fiducial touch-points comprises first identifying fiducial touch-points on images, as indicated by block 342, touching the fiducial touch-points with a tracked instrument, as indicated by block 344, and determining registration data in relation to reference markers, as indicated by block 346. The method M1 alternatively further comprises: completing registration by conducting a surface scan procedure, as indicated by block 350, wherein conducting a surface scan procedure comprises scanning the face using a 3D scanner, as indicated by block 352, extracting the face surface data from MR/CT data, as indicated by block 354, and determining registration data points by matching the face surface data from the 3D scanner with the face surface data from MR/CT data, as indicated by block 356. Upon completing registration by using fiducial touch-points procedure, as indicated by block 340, or surface scan completing registration by conducting a surface scan procedure, as indicated by block 350, and transforming and confirming the determined registration data, as indicated by block 308.

Still referring to FIG. 3B, during a navigation procedure, such via the method M1, a handheld instrument is trackable by using a tracking system 213, and a representation of the instrument's position and orientation may be provided and displayed as an overlay on a previously acquired or current image (such as a three-dimensional scan) of a patient's anatomy obtained with an imaging device or system (such as ultrasound, CT or MRI). To achieve this, a registration is needed between the coordinate frame of a tracking system 213, the physical location of the patient 102 in space, and the coordinate frame of the corresponding image of the patient 102. This registration is typically obtained relative to a tracked reference marker, which is placed in a fixed position relative to the patient anatomy of interest and thus can be used as a fixed reference for the anatomy. Generally, this can be accomplished by attaching the reference to a patient immobilization frame (such as a clamp for skull fixation in neurosurgery), which itself is rigidly attached to the patient 102. However, the reference may be held to the frame, for example, through an arm, which can be bumped and accidentally moved, which creates a loss of registration.

Still referring to FIG. 3B, additionally, since the reference marker must be positioned so that it is visible by the navigation hardware (typically requiring line-of-sight for optical tracking, or otherwise within the observation or communication field of the tracking system 213), this tends to position the reference such that it is in the open thus more susceptible to accidental interaction and loss of registration. In situations of lost registration, a surgical procedure tends to be stopped while a new registration is computed, although this may not always be possible if, for example, the registration fiducial-points or patient skin surface are no longer accessible due to the progression of the surgical procedure, and thus creating a need for a full re-registration or, in some cases even disabling navigation for the remainder of the procedure.

Still referring to FIG. 3B and referring back to FIG. 3A, in the method M1, after confirming registration, as indicated by block 308, draping the patient 102, as indicated by block 310, comprises covering the patient 102 and surrounding areas with a sterile barrier (not shown) to create and maintain a sterile field during the surgical procedure. The purpose of the draping step is to eliminate the passage of microorganisms, e.g., bacteria, between non-sterile and sterile areas. After performing the draping step, as indicated by block 310, the method M1 comprises confirming patient engagement points, as indicated by block 312, and preparing and planning the craniotomy, as indicated by block 314 (FIG. 4C).

Figure 4A:
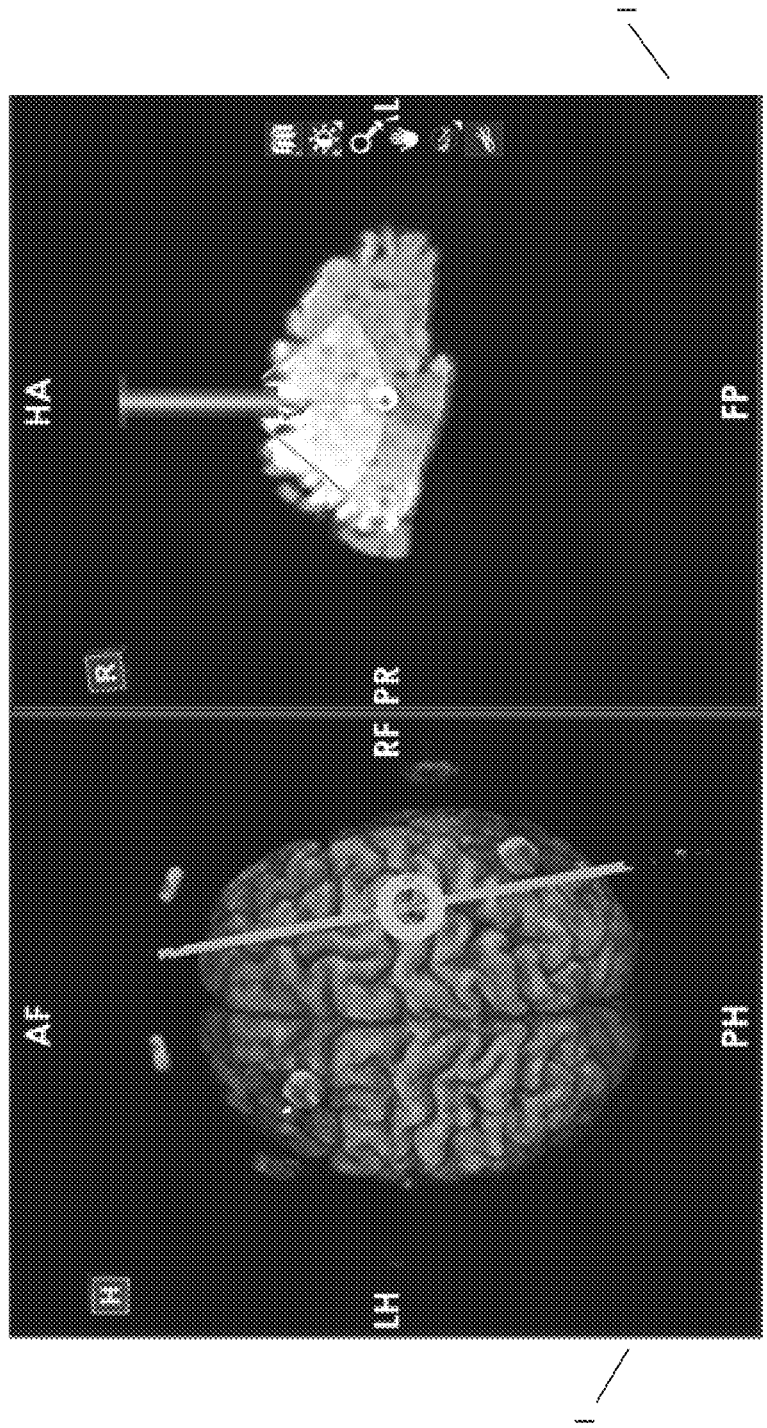
FIG. 4A is a screenshot illustrating at least one image of a brain renderable on a display device during a step of a positioning and fixing step in the method, as shown in FIGS. 3A and 3B, by way of a navigation system, in accordance with an embodiment of the present disclosure.
Figure 4B:
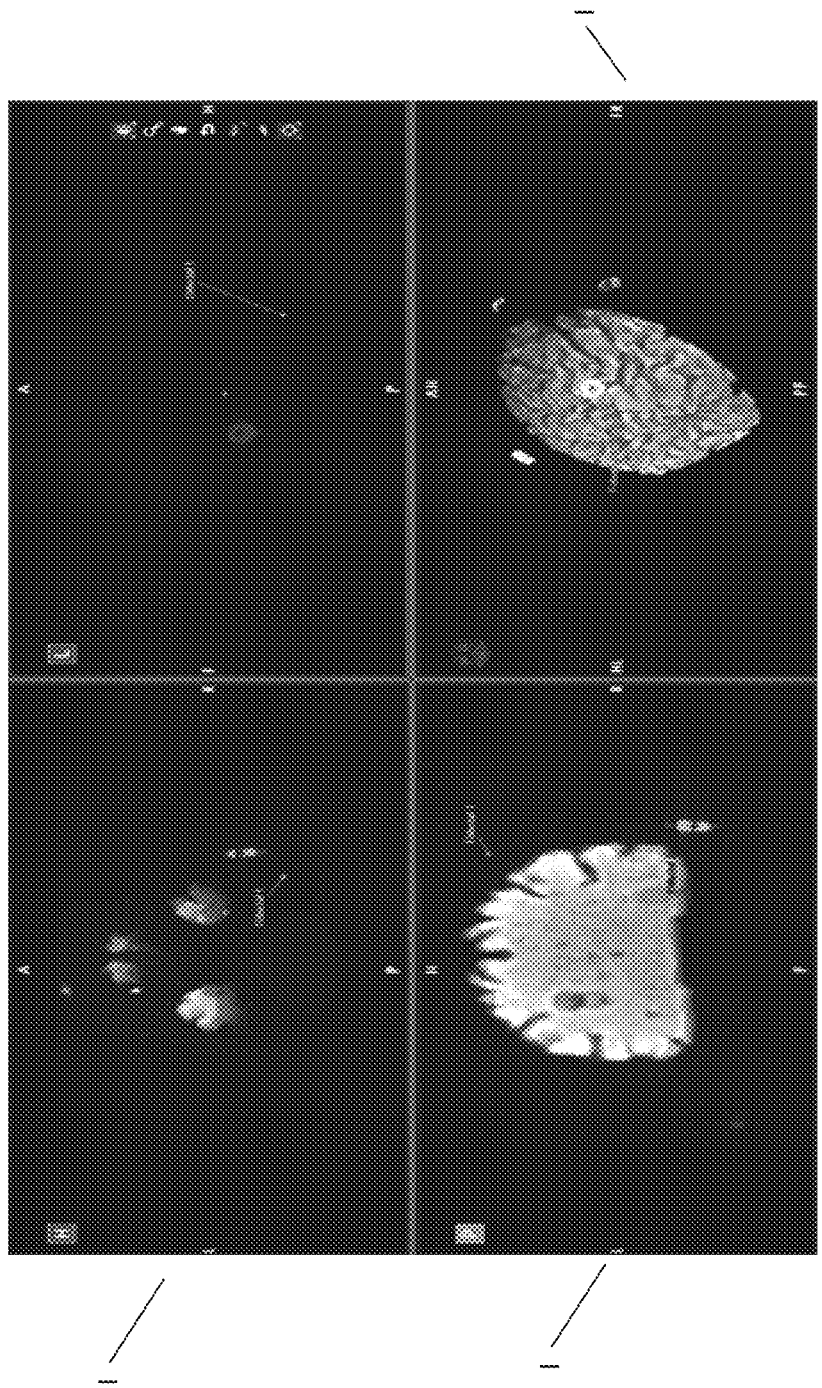
FIG. 4B is a screenshot illustrating at least one image of a brain renderable on a display device during a step of initiating registration, e.g., by using fiducial touch-points, in the method, as shown in FIGS. 3A and 3B, by way of a navigation system, in accordance with an embodiment of the present disclosure.
Figure 4C:
FIG. 4C is a screenshot illustrating at least one image of a brain renderable on a display device during a step of preparing and planning a craniotomy, in the method, as shown in FIGS. 3A and 3B, by way of a navigation system, in accordance with an embodiment of the present disclosure.
Figure 4D:
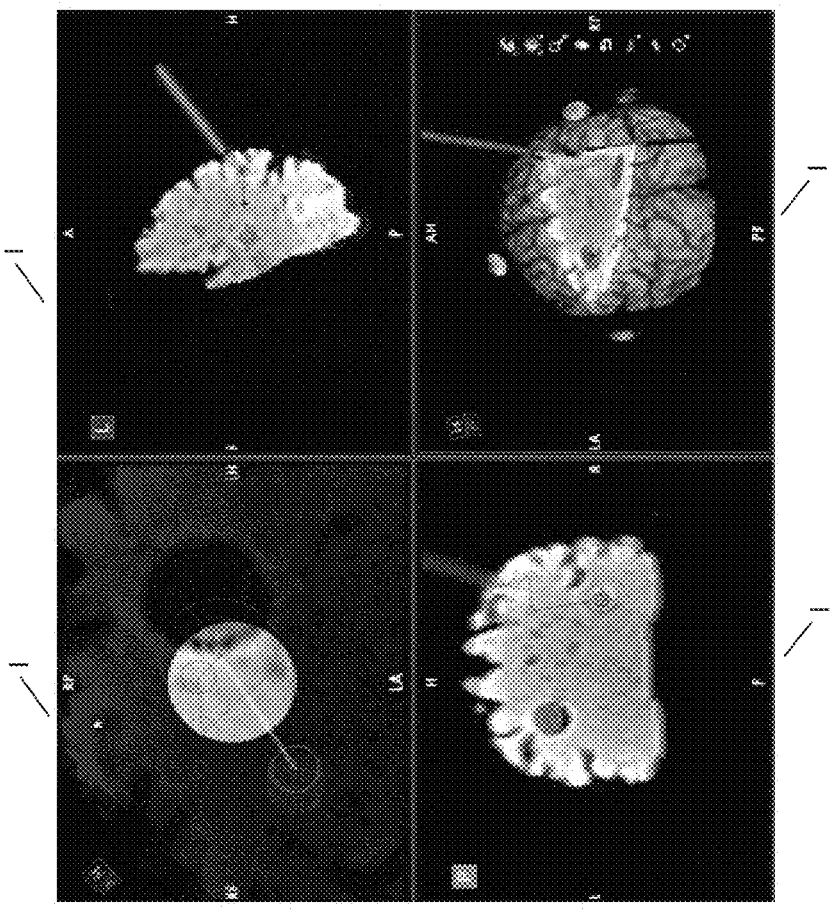
FIG. 4D is a screenshot illustrating at least one image of a brain renderable on a display device during steps of confirming engagement and motion range within a cranial space and cutting a dura at the engagement point and identifying a sulcus, in the method, as shown in FIGS. 3A and 3B, by way of a navigation system, in accordance with an embodiment of the present disclosure.
Figure 4D:
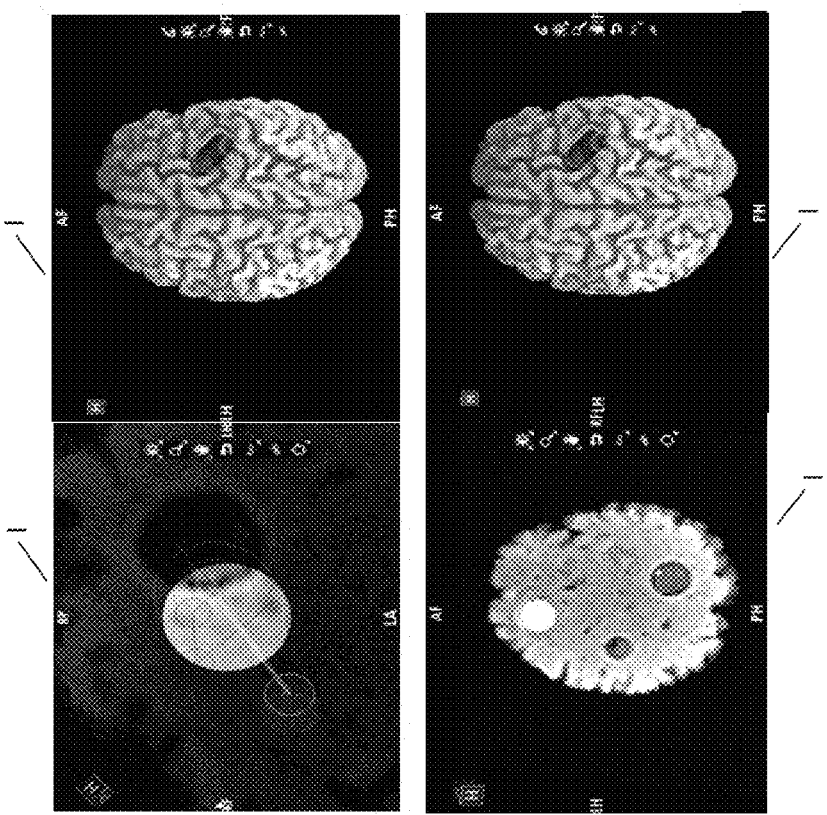

Still referring to FIG. 3B and referring back to FIG. 3A, in the method M1, after preparing and planning the craniotomy, as indicated by block 314, the method M1 comprises cutting the cranium e.g., by way of a craniotomy, wherein a bone flap is temporarily removed from the skull to access the brain 102b, as indicated by block 316, updating registration data, as indicated by block 322, such as by adding additional registration correspondence points within the craniotomy, e.g. the location of a visible blood vessel, confirming the engagement within the craniotomy location and the motion range, as indicated by block 318, and cutting the dura at the engagement points and identifying the sulcus, as indicated by block 320 (FIG. 4D).

Still referring to FIG. 3B and referring back to FIG. 3A, the method M1 also comprises updating the registration data, as indicated by block 322, wherein updating comprises adding further registration correspondence points near the engagement point, e.g. a bifurcation of the entry sulcus. In an embodiment of the present disclosure, by focusing the wide field camera's gaze on the surgical area of interest, updating the registration data comprises manipulating or transforming the registration data to ensure the best match for the surgical area of interest, while ignoring any non-uniform tissue deformation affecting areas outside of the surgical area of interest. Additionally, by matching overlay representations of tissue with an actual view of the tissue of interest, the particular tissue representation can be matched to the video image, thereby tending to ensure registration of the tissue of interest.

Still referring to FIG. 3B and referring back to FIG. 3A, in the method M1, for example, matching overlay representations of tissue with an actual view of the tissue of interest is automatically performable by at least one of: (a) matching a video of a post craniotomy brain, e.g., an exposed brain, with an imaged sulcal map; (b) matching a video position of exposed vessels with image segmentation of vessels; (c) matching a video position of a lesion or a tumour with an image segmentation of a tumour; and (d) matching a video image from an endoscopy up-nasal cavity with a bone rendering of a bone surface on a nasal cavity for an endonasal alignment. The method M1 further comprises using multiple cameras and overlaying images with tracked instrument(s) views, thereby allowing multiple views of the data and overlayed images to be simultaneously presented, e.g., in real-time, thereby improving registration or correction.

Figure 4E:
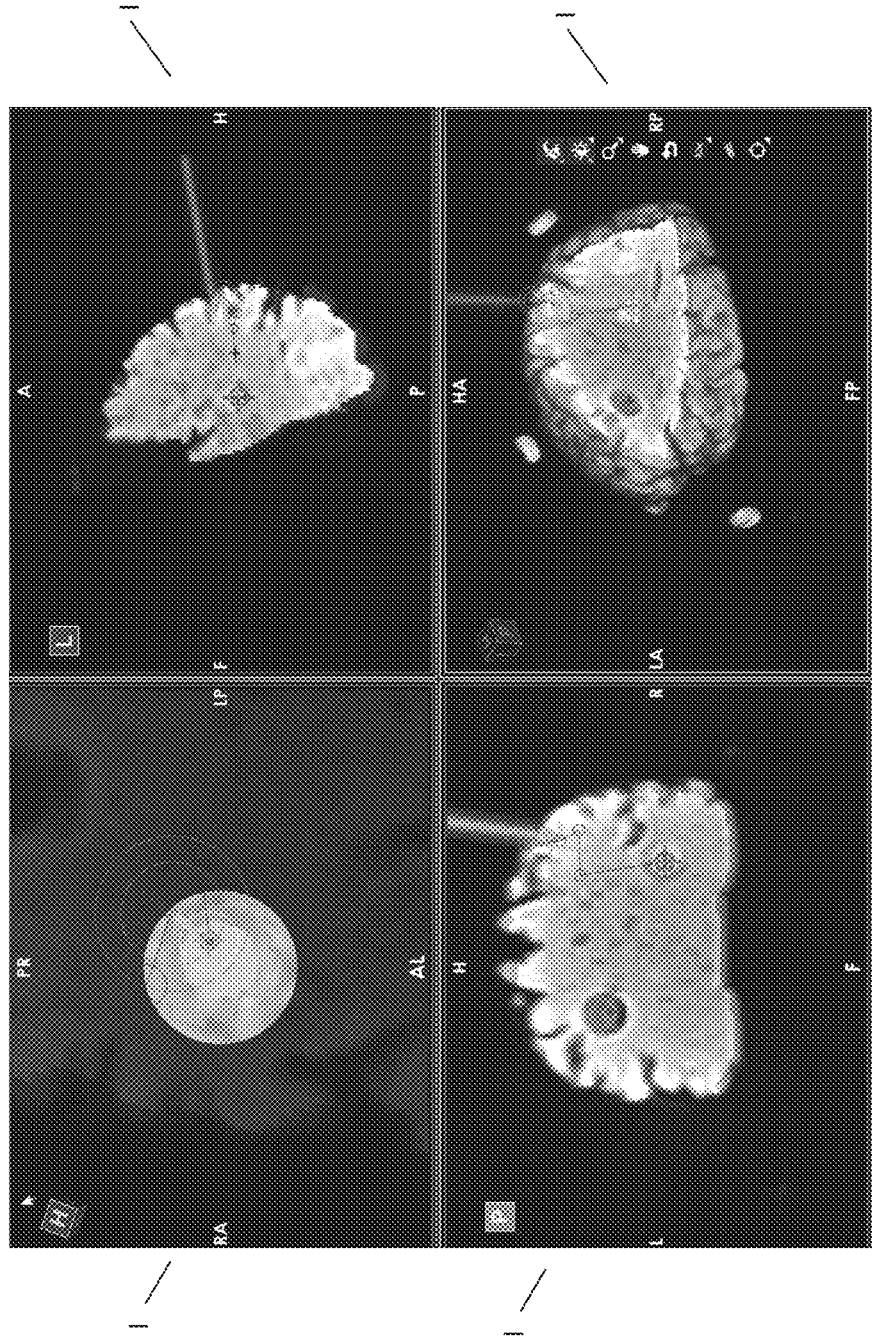
FIG. 4E is a screenshot illustrating at least one image of a brain renderable on a display device during iterative cannulating steps, in the method, as shown in FIGS. 3A and 3B, by way of a navigation system, in accordance with an embodiment of the present disclosure.

Still referring to FIG. 3B and referring back to FIG. 3A, in the method M1, completing the planned trajectory, as indicated by block 324, comprises initiating cannulation, wherein cannulation comprises inserting a port (not shown) into the brain 102b, typically along a sulci path after identifying sulci, as indicated by block 320, along a planned trajectory. Cannulation is an iterative process that involves repeating the steps of aligning the port on engagement and setting the planned trajectory, as indicated by block 332, and then cannulating to the target depth, as indicated by block 334, until the planned trajectory is completed, as indicated by block 324 (FIG. 4E).

Still referring to FIG. 3B and referring back to FIG. 3A, in the method M1, the iterative cannulation process, as indicated by blocks 324, 332, 334, together, may also support multi-point trajectories where a target, e.g., a tumour, is accessible by pushing to intermediate points, then adjusting the angle to get to the next point in planned trajectory. This process allows trajectories to be redefined around tissue that one may want to preserve, or ensure that the trajectory stays within a sulcus to avoid damaging neighbouring tissue, e.g., healthy tissue. Navigating multi-point trajectories may be accomplished by physically reorienting a straight port at different points along a (planned) path, or by having a flexible port that has a number of manipulable bends that can be set along the path.

Still referring to FIG. 3B and referring back to FIG. 3A, in the method M1, decannulating, as indicated by block 326, comprises: removing the access port 206 and any tracking instruments from the brain 102b; resecting by removing at least one of a part of the brain 102b and a tumour of interest, as indicated by block 328; and closing the dura and closing the cranium, thereby completing the craniotomy, as indicated by block 330. In a further embodiment of the present disclosure, the method M1, using the navigation system 200, further comprises at least one of imaging, re-imaging, and registering, by using different modalities, fiber structures of the brain, such as nerves, ligaments, etc., for intra-operatively addressing (avoiding) such fiber structures.

Referring to FIG. 4A, this screenshot illustrates at least one image I of a brain 102b renderable on a display device 205 during a step of positioning and fixing a patient 102, as indicated by block 304, in the method M1, as shown in FIGS. 3A and 3B, by way of a navigation system 200, in accordance with an embodiment of the present disclosure. In FIG. 4A at least one image I are renderable during the step of positioning and fixing the patient 102, as indicated by block 304, wherein positioning is performed in response to instructions from the navigation software, and wherein positioning comprises at least one of reviewing the imported surgical plan, confirming whether a patient positioning is consistent with craniotomy needs, and selecting a planned trajectory from a list of planned trajectories corresponding to the imported surgical plan.

Referring to FIG. 4B, this screenshot illustrates at least one image I of a brain 102b renderable on a display device 205 during execution of an initiating registration 400 of a brain 102b, e.g., by using fiducial touch-points, in the method M1, as shown in FIGS. 3A and 3B, by way of a navigation system 200, operable in response to instructions from navigation software, in accordance with an embodiment of the present disclosure.

Referring to FIG. 4C, this screenshot illustrates at least one image I of a brain 102b renderable on a display device 205 during a step of preparing and planning a craniotomy, as indicated by block 306, in the method M1, as shown in FIGS. 3A and 3B, by way of a navigation system 200, operable in response to instructions from navigation software, in accordance with an embodiment of the present disclosure.

Referring to FIG. 4D, this screenshot illustrates at least one image I of a brain 102b renderable on a display device 205 during steps of confirming engagement and motion range within a cranial space, as indicated by block 318, and cutting a dura at the engagement point and identifying a sulcus, as indicated by block 320, in the method M1, as shown in FIGS. 3A and 3B, by way of a navigation system 200, operable in response to instructions from navigation software, in accordance with an embodiment of the present disclosure.

Referring to FIG. 4E, this screenshot illustrates at least one image I of a brain 102b renderable on a display device 205 during iterative cannulating steps, as indicated by blocks 324, 332, 334, together, in the method M1, as shown in FIGS. 3A and 3B, by way of a navigation system 200, operable in response to instructions from navigation software, in accordance with an embodiment of the present disclosure.

Figure 5:
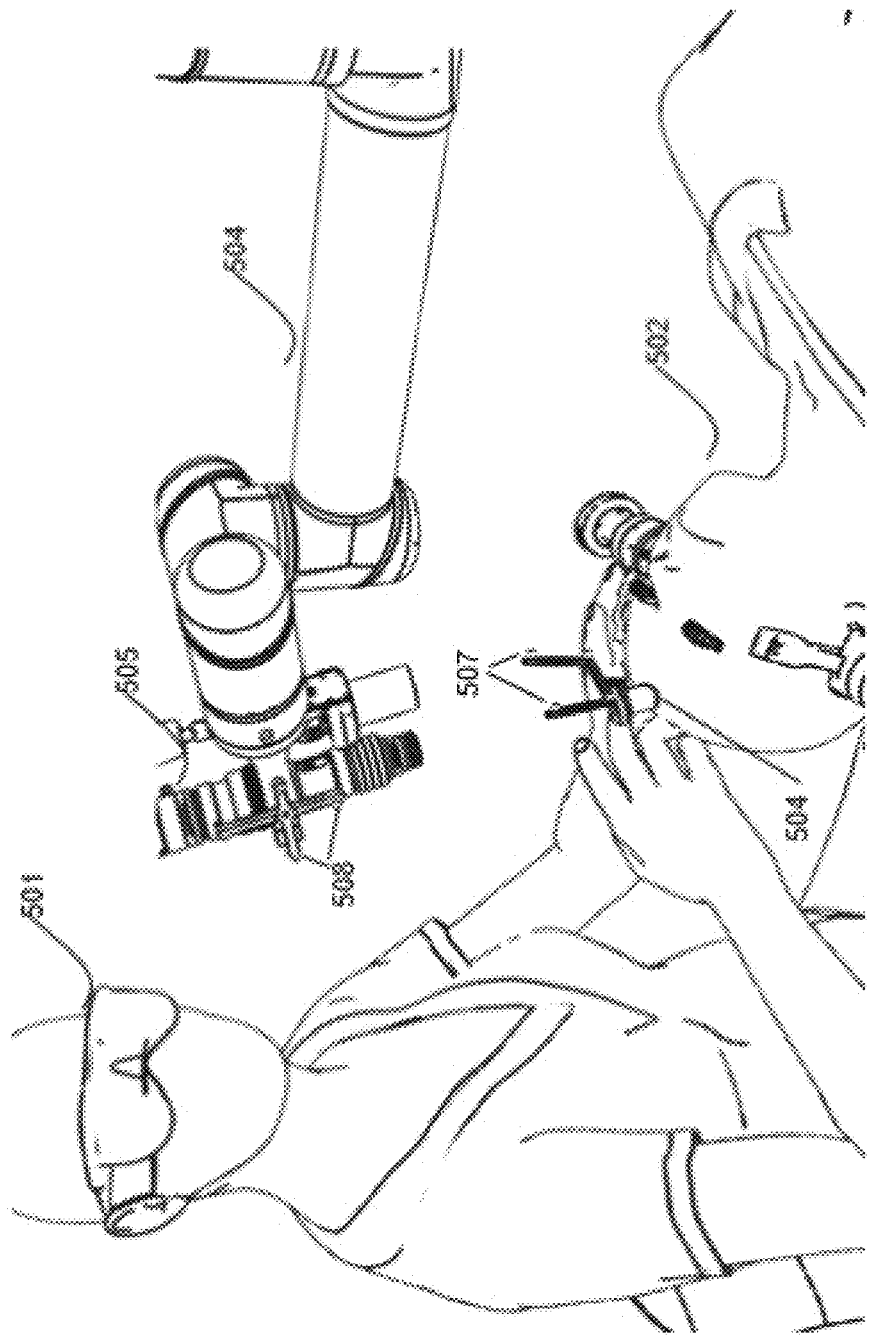
FIG. 5 is a diagram illustrating an access port based surgical procedure being conducted by way of the navigation system and methods, in accordance with some embodiments of the present disclosure.

Referring to FIG. 5, this diagram illustrates a access port based surgical procedure being conducted by way of the navigation system 200 and methods, such as the method M1, in accordance with some embodiments of the present disclosure. In this example, a surgeon 501 is resecting a tumor from the brain 102b of a patient 502 through an access port 506. An external scope 505 is coupled with a robotic arm 504, and is used to view down port 506 at a sufficient magnification to allow for enhanced visibility down port 506. The output of external scope 505 is rendered on a visual display, such as the display device 205.

Still referring to FIG. 5, the method M1, as shown in FIGS. 3A and 3B, may further comprise a step of quantitatively registering that least one image I by way of the system 200, wherein quantitatively registering comprises measuring at least one absolute quantitative metric and using that absolute quantitative metric to register images among a plurality of imaging modalities, thereby providing transformed imaging data. The at least one absolute quantitative metric comprises at least one of T1, T2, cell density, tissue density, tissue anisotropy, tissue stiffness, fluid flow per volume or area, electrical conductivity, pH, and pressure. The method M1 further comprises disposing active or passive fiduciary markers, respectively, 507, 508, e.g., spherical markers, in relation to at least one of the access port 506 and the external scope 505 for facilitating their tracking (location of these tools) by the tracking system 213. The active or passive fiduciary markers, 507, 508, are sensed by sensors of the tracking system 213, whereby identifiable points are provided. A tracked instrument is typically indicated by a sensing a grouping of active or passive fiduciary markers, 507, 508, whereby a rigid body, such as a tool, such as a tracking tool, is identified by the tracking system 213, and whereby the position and pose in 3D of a tracked instrument, such as a tool, is determinable. Typically, a minimum of 3 active or passive fiduciary markers, 507, 508, are placed on a tracked tool to define the instrument. In the several figures of the Drawing, four active or passive fiduciary markers, 507, 508, are used to track each tool, by example only.

Still referring to FIG. 5, in a preferred embodiment, the navigation system 200 may comprise fiduciary markers, the fiduciary markers comprising reflectosphere markers in combination with an optical tracking system to determine spatial positioning of the surgical instruments within the operating field. The spatial position of automated mechanical arm(s) or robotic arms used during surgery may be also tracked in a similar manner. Differentiation of the types of tools and targets and their corresponding virtual geometrically accurate volumes could be determined by the specific orientation of the reflectospheres relative to one another giving each virtual object an individual identity within the navigation system. The individual identifiers would relay information to the system as to the size and virtual shape of the tool within the system. The identifier could also provide information such as the tools central point, the tools central axis, etc. The virtual tool may also be determinable from a database of tools provided to the navigation system 200. The marker positions could be tracked relative to an object in the operating room such as the patient. Other types of markers that could be used would be RF, EM, LED (pulsed and un-pulsed), glass spheres, reflective stickers, unique structures and patterns, wherein the RF and EM would have specific signatures for the specific tools to which they would be attached. The reflective stickers, structures, and patterns, glass spheres, LEDs could all be detected using optical detectors, while RF and EM could be detected by using antennas. Advantages to using EM and RF tags would include removal of the line of sight condition during the operation, where using optical system removes the additional noise from electrical emission and detection systems.

Still referring to FIG. 5, in a further embodiment, printed or 3-D design markers could be used for detection by an auxiliary camera and/or external scope. The printed markers could also be used as a calibration pattern to provide distance information (3D) to the optical detector. These identification markers may include designs such as concentric circles with different ring spacing, and/or different types of bar codes. Furthermore, in addition to using markers, the contours of known objects (e.g., side of the port, top ring of the port, shaft of pointer tool, etc.) could be made recognizable by the optical imaging devices through the tracking system 213.

Referring to FIG. 6A, this diagram illustrates, in a perspective view, a patient reference device D1 comprising a tracking tool, such as a pointing tool 600, in accordance with an embodiment of the present disclosure. The patient reference device D1 further comprises a tracking marker 610 disposed on a connector beam 615 attached to an arm 620 of a pointing tool 600. A minimum of three (3) tracking markers 610, and preferably four (4) tracking markers 610, facilitate tracking the device D by the tracking system 213.

Referring to FIG. 6B, this diagram illustrates, in a perspective view, a patient reference device D1 comprising a tracking tool 640, in accordance with an embodiment of the present disclosure. The tracking tool 640 is coupled with a supporting arm structure 642 to which four tracking markers 610 are rigidly attached.

Figure 6C:
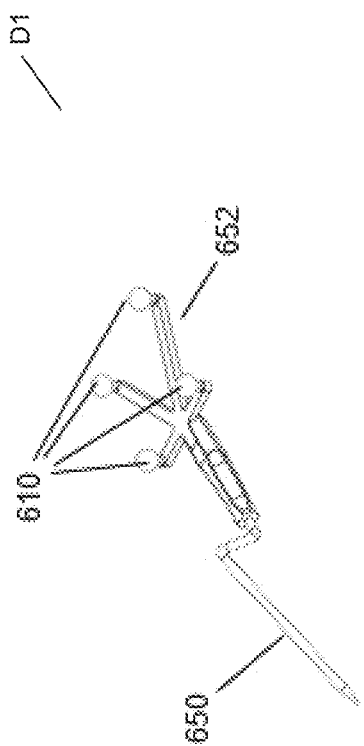
FIG. 6C is a diagram illustrating a perspective view of a patient reference device comprising a tracking tool, in accordance with an embodiment of the present disclosure.

Referring to FIG. 6C, this diagram illustrates, in a perspective view, a patient reference device D1 comprising a tracking tool 650, in accordance with an embodiment of the present disclosure. The tracking tool 650 is coupled with a supporting arm structure 652 to which four tracking markers 610 are rigidly attached.

Figure 6D:
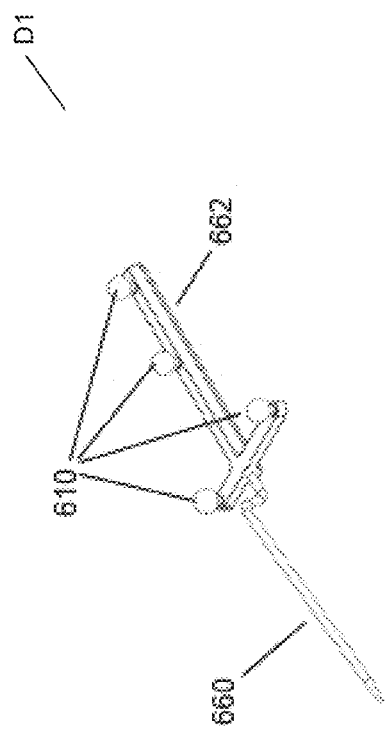
FIG. 6D is a diagram illustrating a perspective view of a patient reference device comprising a tracking tool, in accordance with an embodiment of the present disclosure.

Referring to FIG. 6D, this diagram illustrates, in a perspective view, a patient reference device D1 comprising a tracking tool 660, in accordance with an embodiment of the present disclosure. The tracking tool 660 is coupled with a supporting arm structure 662 to which four tracking markers 610 are rigidly attached.

Figure 6E:
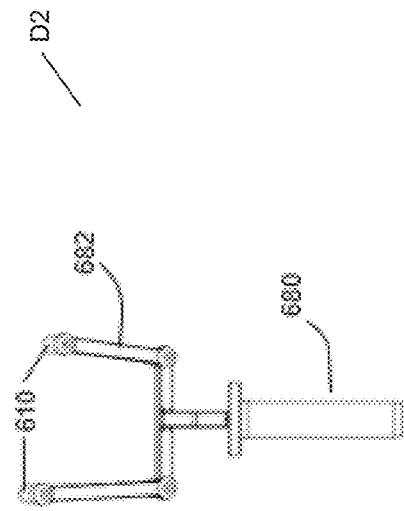
FIG. 6E is a diagram illustrating a perspective view of a patient reference device comprising an access port, in accordance with an embodiment of the present disclosure.

Referring to FIG. 6E, this a diagram illustrates, in a perspective view, a patient reference device D2 comprising an access port 680, in accordance with an embodiment of the present disclosure. The patient reference device D2 further comprises "fiducial," fiducial marker, or tracking markers 610 placed on an extended arm 682 that is firmly attached to the access port 680. This arrangement enables clear visibility of the "fiducial," fiducial marker, or tracking markers 610 to the tracking system 213. Further, the extended arm 682 ensures that the "fiducial," fiducial marker, or tracking markers 610 do not interfere with surgical tools that may be inserted through the access port 680. The non-uniform structure of the extended arm 682 for the tracking markers 610 enables the tracking system 213 to discern both the position and orientation of the access port 680 in response to instructions corresponding to the tracking software.

Figure 6F:
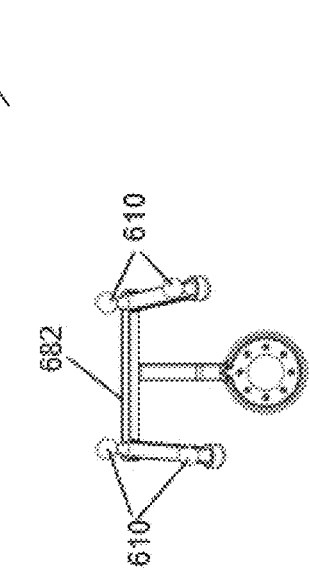
FIG. 6F is a diagram illustrating a front view of a patient reference device comprising an access port, as shown in FIG. 6E, in accordance with an embodiment of the present disclosure.

Referring to FIG. 6F, this diagram illustrates, in a front view, a patient reference device D2 comprising an access port 680, as shown in FIG. 6E, in accordance with an embodiment of the present disclosure.

Figure 6G:
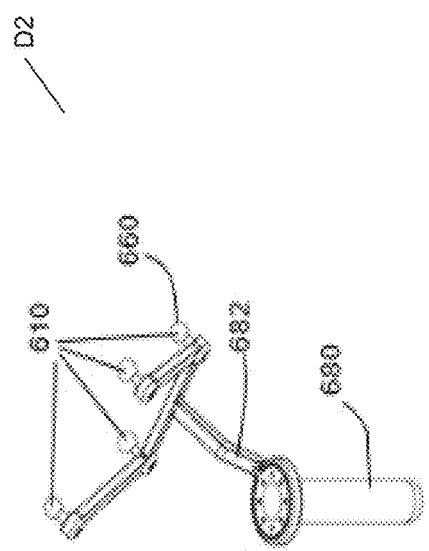
FIG. 6G is a diagram illustrating a side view of a patient reference device comprising an access port, as shown in FIG. 6E, in accordance with an embodiment of the present disclosure.

Referring to FIG. 6G, this diagram illustrates, in a side view, a patient reference device D2 comprising an access port 680, as shown in FIG. 6E, in accordance with an embodiment of the present disclosure.

Figure 6H:
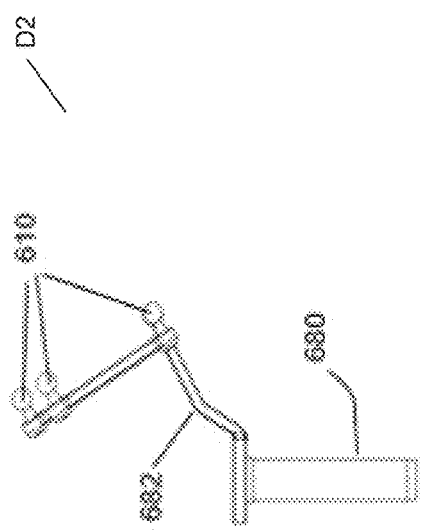
FIG. 6H is a diagram illustrating a top view of a patient reference device comprising an access port, as shown in FIG. 6E, in accordance with an embodiment of the present disclosure.

Referring to FIG. 6H, this diagram illustrates, in a top view, a patient reference device D2 comprising an access port 680, as shown in FIG. 6E, in accordance with an embodiment of the present disclosure.

Figure 7:
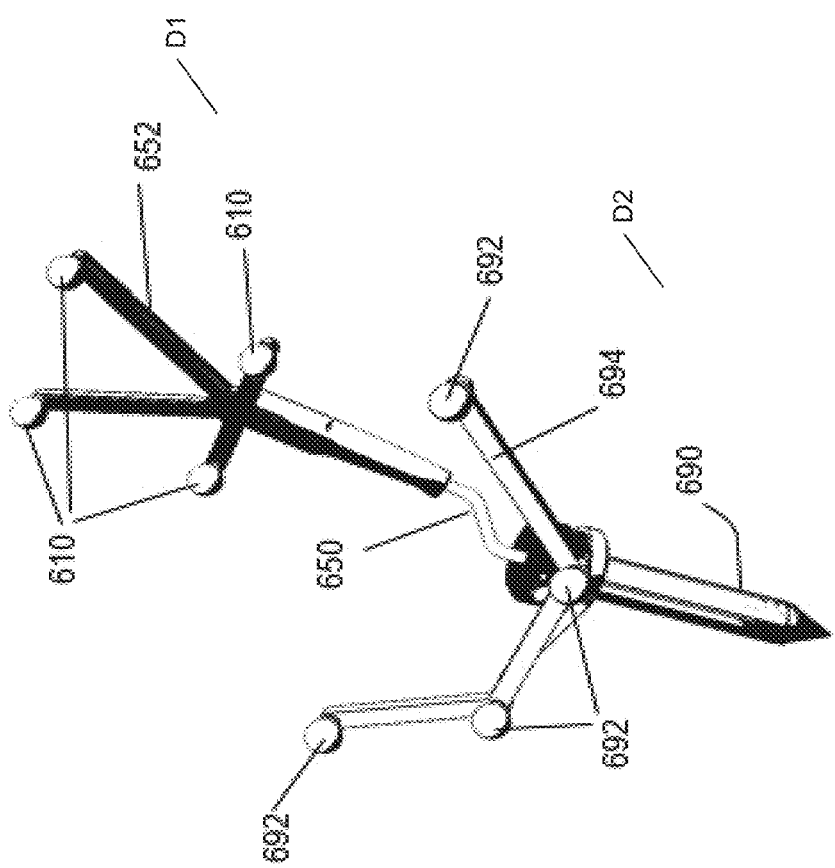
FIG. 7 is a diagram illustrating a perspective view of a patient reference device comprising a tracking tool, as shown in FIG. 6C, engaged with a patient reference device comprising an access port, in accordance with an embodiment of the present disclosure.

Referring to FIG. 7, this diagram illustrates, in a perspective view, a patient reference device D1 comprising a tracking tool 650, such as a pointing tool, as shown in FIG. 6C, engaged with a patient reference device D2 comprising an access port 690, with an embodiment of the present disclosure. The patient reference device D1 comprises the tracking tool 650, an associated support arm structure 652 (FIG. 6C) with associated "fiducial," fiducial marker, or fiducial markers 610, inserted into a port 690 of the patient tracking device D2 further comprising "fiducials" or fiducial markers 692 on associate arm support structure 694. Both the tracking tool 650 and the access port 690 are equipped with respective arms 652, 694 configured with respective tracking markers 610, 692. These patient reference devices D1, D2 with respective tracking markers 610, 692 are separately trackable by the tracking system 213 of the navigation system 200 and are differentiable as unique objects in images rendered on the display device 205.

Figure 8:
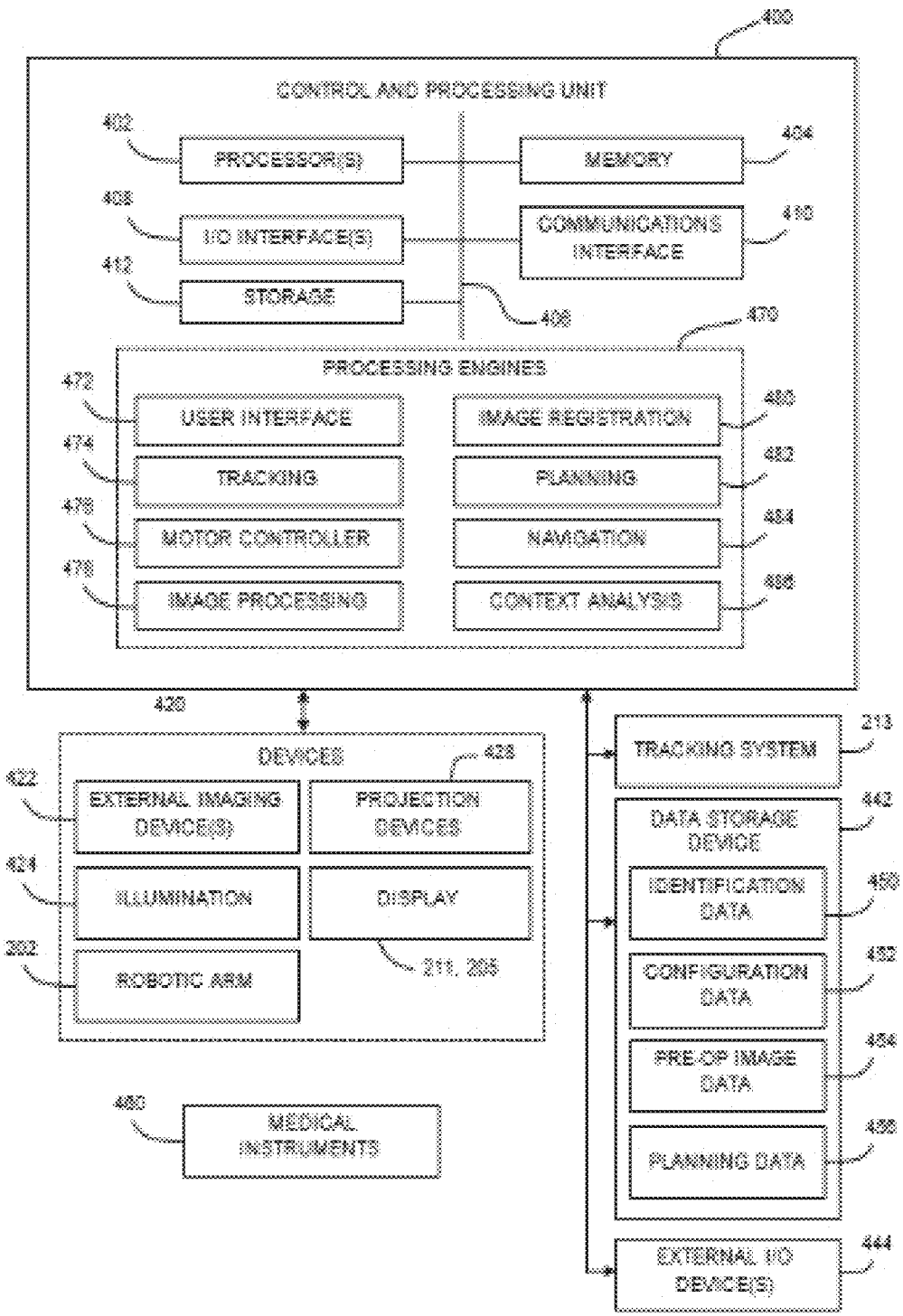
FIG. 8 is a schematic diagram illustrating a relationship between components of the navigation system, such as a control and processing unit, a tracking system, a data storage device for the tracking system, and system devices, and medical instruments, in accordance with an embodiment of the present disclosure.

Referring to FIG. 8, this schematic diagram illustrates a relationship between components of the navigation system 200, such as a control and processing unit 400, a tracking system 213, a data storage device 442 for the tracking system 213, and system devices 420, and medical instruments 460, in accordance with an embodiment of the present disclosure. The control and processing unit 400 comprises at least one processor 402, a memory 404, such as a non-transitory memory device, a system bus 406, at least one input/output interface 408, a communications interface 410, and storage device 412. The control and processing unit 400 is interfaced with other external devices, such as the tracking system 213, data storage 442 for the tracking system 213, and external user input and output devices 444, optionally comprising, for example, at least one of a display device, such as display devices 211, 205, a keyboard, a mouse, a foot pedal, a microphone, and a speaker.

Still referring to FIG. 8, the data storage 442 comprises any suitable data storage device, such as a local or remote computing device, e.g. a computer, hard drive, digital media device, or server, having a database stored thereon. The data storage device 442 includes identification data 450 for identifying at least one medical instrument 460 and configuration data 452 for associating customized configuration parameters with at least one medical instrument 460. The data storage device 442 further comprises at least one of preoperative image data 454 and medical procedure planning data 456. Although data storage device 442 is shown as a single device, understood is that, in other embodiments, the data storage device 442 comprises multiple storage devices. The data storage device 442 is also configured to store data in a custom data structure corresponding to various 3D volumes at different resolutions, each be captured with a unique time-stamp and/or quality metric. This custom data structure provides the system 200 with an ability to move through contrast, scale, and time during the surgical procedure.

Still referring to FIG. 8, medical instruments 460 are identifiable by the control and processing unit 400, wherein the medical instruments 460 are coupled with, and controlled by, the control and processing unit 400. Alternatively, the medical instruments 460 are operable or otherwise independently employable without the control and processing unit 400. The tracking system 213 may be employed to track at least one of medical instruments 460 and spatially register the at least one of medical instrument 460 in relation to an intra-operative reference frame. The control and processing unit 400 is also interfaceable with a number of configurable devices, and may intra-operatively reconfigure at least one such device based on configuration parameters obtained from configuration data 452. Examples of devices 420 include, but are not limited to, at least one external imaging device 422, at least one illumination device 424, robotic arm 202, at least one projection devices 428, and at least one display device, such as display devices 211, 205.

Still referring to FIG. 8, the control and processing unit 400 is operable by the at least one processor 402 and the at least one memory 404. For example, the functionalities described herein are at least partially implemented via hardware logic in processor 402 by way of the instructions stored in memory 404 though at least one processing engine 470. Examples of processing engines 470 include, but are not limited to, user interface engine 472, tracking engine 474, motor controller 476, image processing engine 478, image registration engine 480, procedure planning engine 482, navigation engine 484, and context analysis module 486. Understood is that the system 200 is not intended to be limited to the components shown in the several figures of the Drawing. One or more components of the control and processing 400 may be provided as an external component or device. In one alternative embodiment, navigation module 484 may be provided as an external navigation system that is integrated with control and processing unit 400.

Still referring to FIG. 8, embodiments of the system 200 may be implemented using processor 402 without additional instructions stored in memory 404. Embodiments may also be implemented using the instructions stored in the memory 404 for execution by one or more general purpose microprocessors. Thus, the disclosure is not limited to a specific configuration of hardware, firmware, and/or software. While some embodiments can be implemented in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device. A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Still referring to FIG. 8, the preceding example embodiments involve systems and methods in which a device is intra-operatively configured based on the identification of a medical instrument. In other example embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with, the current phase or step of the medical procedure. In another example, a context measure may identity the medical procedure, or the type of medical procedure, that is being performed. In another example, a context measure may identify the presence of a tissue type during a medical procedure. In another example, a context measure may identify the presence of one or more fluids, such as biological fluids or non-biological fluids (e.g. wash fluids) during the medical procedure, and may further identify the type of fluid. Each of these examples relate to the image-based identification of information pertaining to the context of the medical procedure.

Still referring to FIG. 8, examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Still referring to FIG. 8, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Still referring to FIG. 8, the navigation system 200 provides tools to the neurosurgeon that will lead to the most informed, least damaging neurosurgical operations. In addition to port-based removal of brain tumours and intracranial hemorrhages (ICH), the navigation system 200 can also be applied to at least one of: (a) a brain biopsy, (b) a functional/deep-brain stimulation, (c) a catheter/shunt placement, (c) an open craniotomies, (d) an endonasal/skull-based/ENT, and (e) spine procedures.

Figure 9:
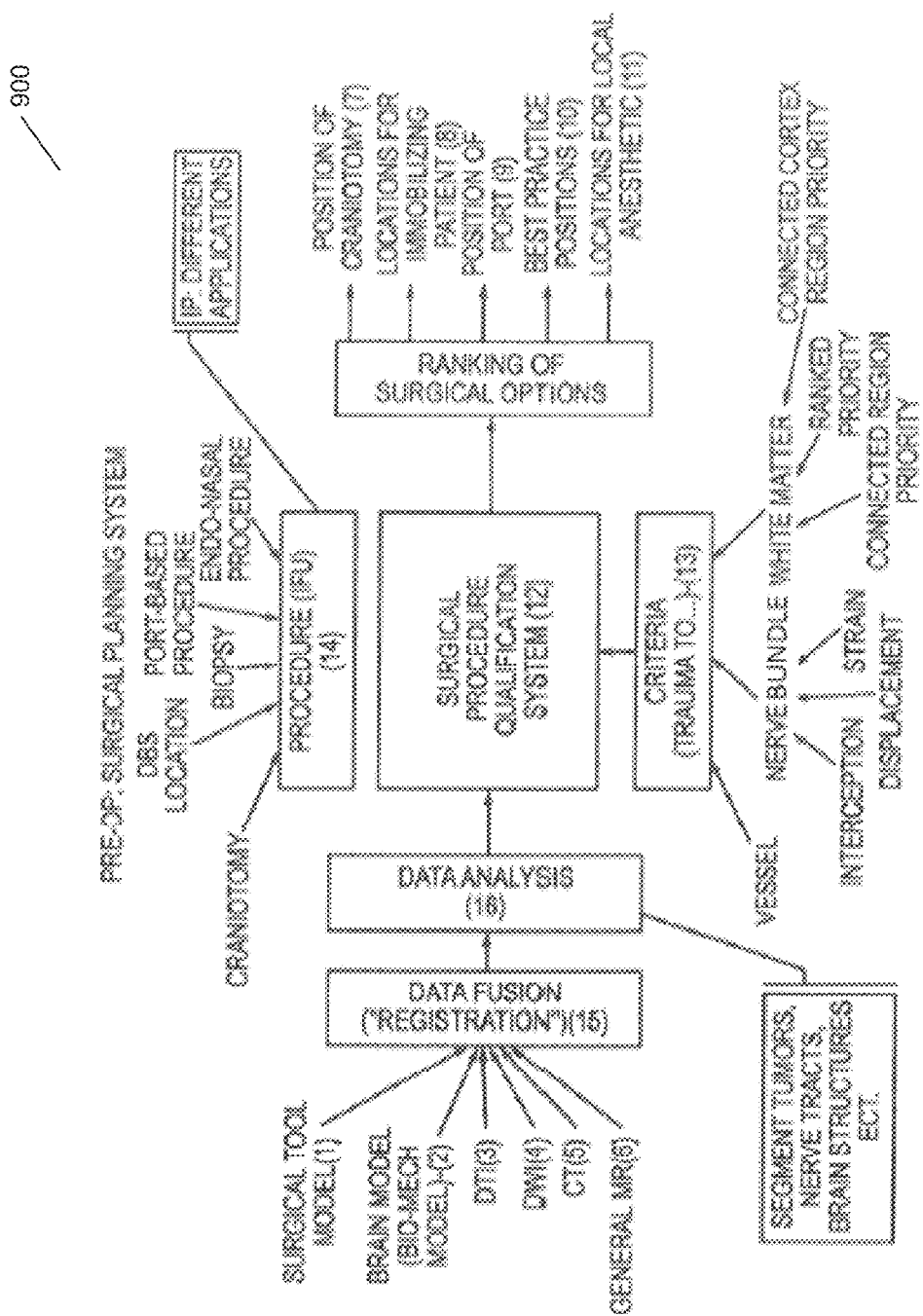
FIG. 9 is a schematic diagram illustrating a pre-operative surgical planning system for use with a medical navigation system, in accordance with an embodiment of the present disclosure.

Referring to FIG. 9, this schematic diagram illustrates a pre-operative surgical planning system 900 for use with a navigation system 200, in accordance with an embodiment of the present disclosure. The pre-operative surgical planning system 900 comprises components and inputs for planning and scoring surgical paths as disclosed herein and as disclosed in at least one priority document.

Figure 10:
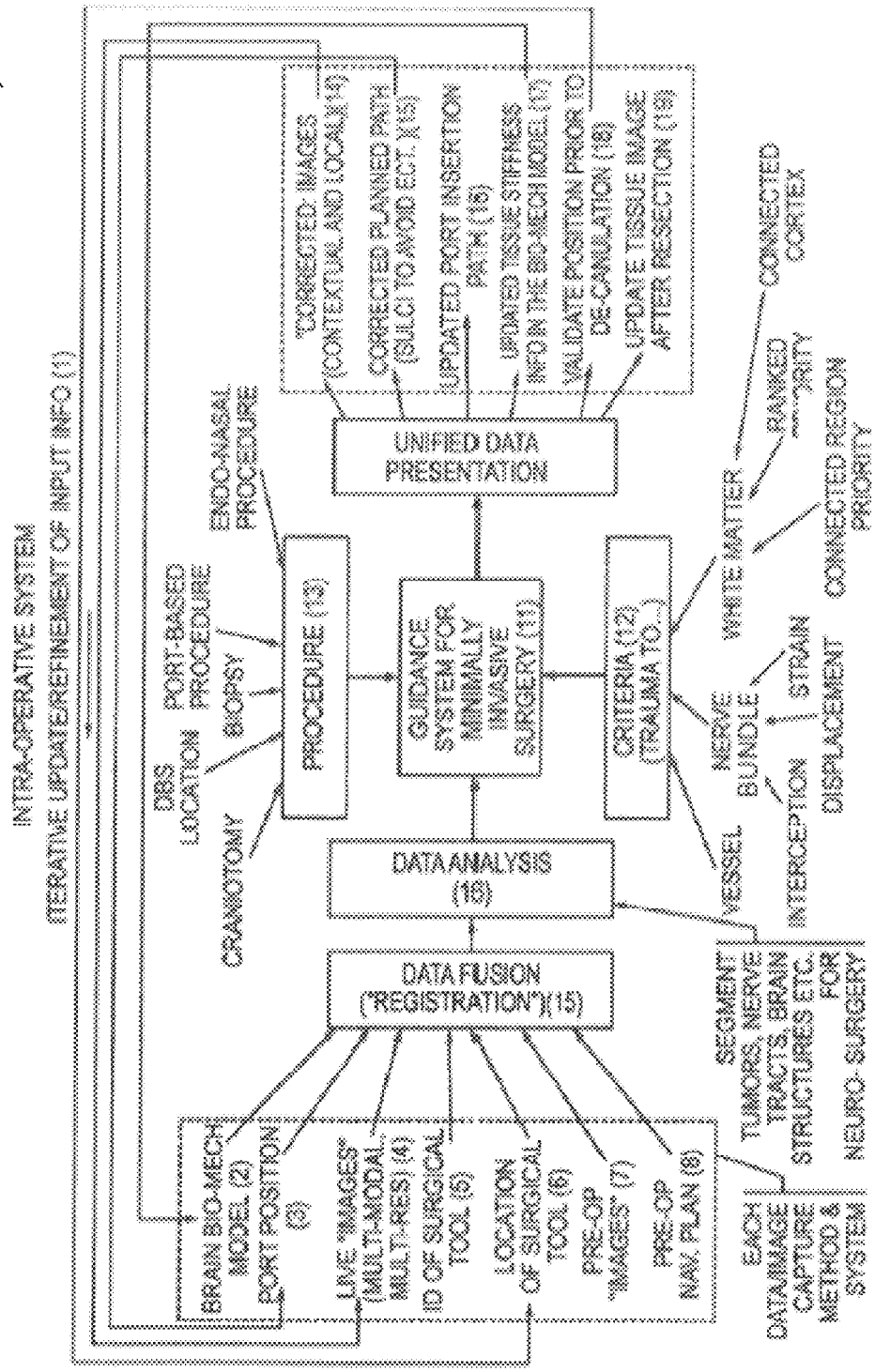
FIG. 10 is a schematic diagram illustrating an intraoperative surgical management system for use with a medical navigation system, in accordance with an embodiment of the present disclosure.

Referring to FIG. 10, this schematic diagram illustrates an intra-operative surgical management system 1000 for use with a navigation system 200, in accordance with an embodiment of the present disclosure. The intra-operative surgical management system 1000 comprises components and inputs for navigation along the surgical paths produced by the pre-operative surgical planning system 900, as shown in FIG. 9. The intra-operative surgical management system 1000 can be used as a surgical planning and navigation tool in the pre-operative and intra-operative stages. Data input(s) of the surgical planning steps and surgical procedures, as shown in FIG. 9, can be used as input(s) to the intra-operative navigation stage performable by the intra-operative surgical management system 1000.

Still referring to FIG. 10, the intra-operative surgical management system 1000 of the navigation system 200 provides a user, such as a surgeon, with a unified technique for navigating through a surgical region by utilizing pre-operative data input(s) and updated intra-operative data input(s). The processor(s), such as the at least one processor 402, is operable by way of a set of instructions 11 and/or algorithms storable in relation to a non-transitory memory device, such as the at least one memory 404, wherein the at least one processor 402 is configured to: analyze pre-operative data input(s) and intra-operative data input(s) and update surgical plans during the course of surgery accordingly.

Still referring to FIG. 10, for example, if intra-operative input(s) in the form of newly acquired images identified a previously unknown or unidentified nerve bundle or a previously unknown or unidentified fiber track, the at least one processor 402 can use these intra-operative input(s), if desired, for updating the surgical plan during surgery to avoid contacting the nerve bundle. The intra-operative input (s) may include a variety input(s), including local data gathered using a variety of sensor(s), such as at least one intra-operative imaging sensor (not shown). In some embodiments, the intra-operative surgical management system 1000 of the navigation system 200 may provide continuously updated, e.g., in real-time, intra-operative input(s) in the context of a specific surgical procedure by way of the at least one intra-operative imaging sensor to: validate tissue position, update tissue imaging after tumor resection, and update surgical device position during surgery.

Still referring to FIG. 10, the intra-operative surgical management system 1000 of the navigation system 200 may provide for re-formatting of the image, for example, to warn of possible puncture of, or collision with, critical tissue structures with a surgical tool during surgery. In addition, the intra-operative surgical management system 1000 may provide imaging and input updates for any shifts or surgical errors that might occur from a needle deflection, tissue deflection, or patient movement as well as provide analysis and transformation of data to correct for imaging distortions, e.g., in real-time. The magnitude of these combined shifts or surgical errors is clinically significant and may regularly exceed 2 cm. Some the most significant are MRI based distortions such gradient non-linearity, susceptibility shifts, eddy current artifacts which may exceed 1 cm on standard MRI scanners (1.5 T and 3.0 T systems). The intra-operative surgical management system 1000 mitigates, and may eliminate, these combined shifts or surgical errors.

Still referring to FIG. 10, in accordance with embodiments of the present disclosure, by using the a intra-operative surgical management system 1000, a variety of intra-operative imaging techniques can be implemented to generate intra-operative input(s) by way of a variety of imaging devices, including anatomy specific MRI devices, surface array MRI scans, endo-nasal MRI devices, anatomy specific US scans, endo-nasal US scans, anatomy specific CT or PET scans, port-based or probe based photo-acoustic imaging, as well as optical imaging done with remote scanning, or probe based scanning, whereby multi-modal imaging and data are providable and transformable into useful images and data in real-time.

Figure 11A:
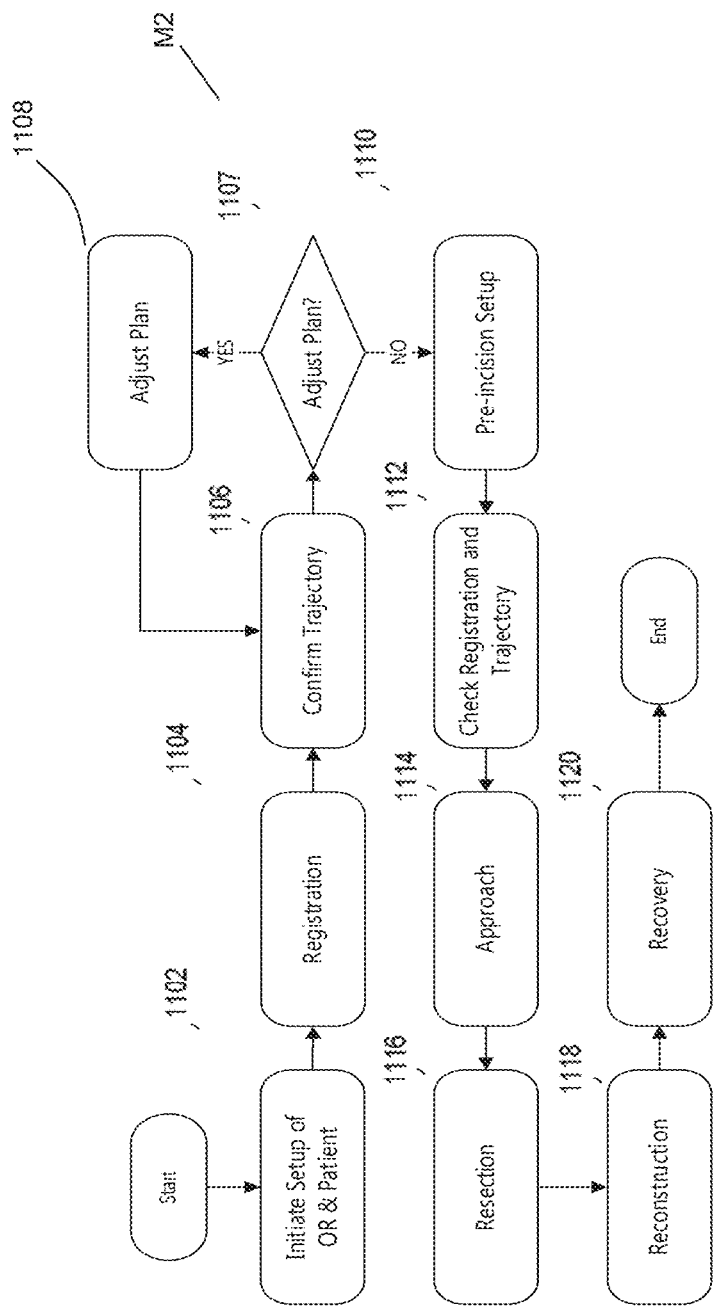
FIG. 11A is a flow diagram illustrating a method of performing a medical procedure, such as a port-based procedure, by way of a navigation system, in accordance with an alternative embodiment of the present disclosure.

Referring to FIG. 11A, this flow diagram illustrates a method M2 of performing a port-based procedure by way of a navigation system 200, in accordance with an alternative embodiment of the present disclosure. The method M2 comprises initiating setup in relation to an OR and a patient 102, as indicated by block 1102, wherein initiating setup comprises setting each piece of relevant equipment, such as lights and surgical tools, in relation to the navigation system 200, and "preparing" and pinning, e.g., by a head clamp, the patient 102 in relation to the headrest; registering a portion of a the patient's anatomy, such as a patient's head 102a, as indicated by block 1104, wherein registering comprises determining a pose of the portion of a the patient's anatomy, e.g., the patient's head 102a, in relation to a base reference frame, and correlating the location of the base reference frame in relation to the imaging frame of reference.

Still referring to FIG. 11A, the method M2 further comprises: confirming the trajectory, as indicated by block 1106, wherein confirming comprises positioning a port, such as the access port 206, is at an engagement point and displaying the trajectory on the at least one display device, such as the display devices 205, 211; determining whether a surgical plan requires adjustment, as indicated by block 1107, wherein determining comprises confirming that each piece of relevant equipment has a sufficient line of sight and reach for the port-based procedure; if an adjustment is required, adjusting the surgical plan based on data comprising at least one observable constraint in the OR, as indicated by block 1108, wherein at least one of a new engagement point and a new target point is defined; if an adjustment is not required, setting pre-incision, as indicated by block 1110, wherein setting pre-incision comprises draping the patient 102 and the relevant equipment and shaving and sterilizing a surgical site of the patient 102; and checking the registration and the trajectory for accuracy, as indicated by block 1112.

Still referring to FIG. 11A, the method M2 further comprises: approaching the surgical site, as indicated by block 1114, wherein approaching comprises commencing a craniotomy by forming a hole in a cranium of the patient head 102a, thereby forming a cranial hole such as by forming a burr-hole, and a bone portion, such as a cranial flap, testing a range of motion of the port, and intra-operatively adjusting the trajectory if required, forming an opening in a dura, thereby forming a dural flap, stitching-back the dural flap, inserting the port, along the trajectory via navigation guidance, such as provided on the at least one display device, and coaxially positioning a surgical camera, such as the optical camera 204, in relation to the port.

Still referring to FIG. 11A, the method M2 further comprises: resecting a target tissue, e.g., immediately after the approaching step, as indicated by block 1116, wherein resecting comprises removing the target tissue, such as a tumour, using a surgical tool, e.g., a NICO Myriad® tool, moving the port within constraints of the cranium hole, e.g., by the surgeon and/or robotics, for facilitating removal of all the target tissue, e.g., by detecting all the target tissue by using immunohistochemistry (ICH) techniques, re-positioning the surgical camera as required for viewing through the port, and cauterizing any tissue having bleeding as required.

Still referring to FIG. 11A, the method M2 further comprises: reconstructing the surgical site, as indicated by block 1118, wherein reconstructing comprises irrigating the surgical site through the port, slowly retracting the port while viewing surgical site via the surgical camera, coupling a graft to at least one portion of the surgical site, e.g., using an adhesive, such as a physiologically compatible glue, unstitching the dural flap, stitching the dural flap into its original position, and redisposing the bone flap into the cranial hole, e.g., by stapling the bone flap; and removing the head clamp; and recovering the patient 102, as indicated by block 1120, wherein recovering the patient 102 comprises sending the patient 102 to a recovery area of a hospital, by example only, and, shortly thereafter, sending the patient 102 home in the absence of any hemorrhage.

Figure 11B:
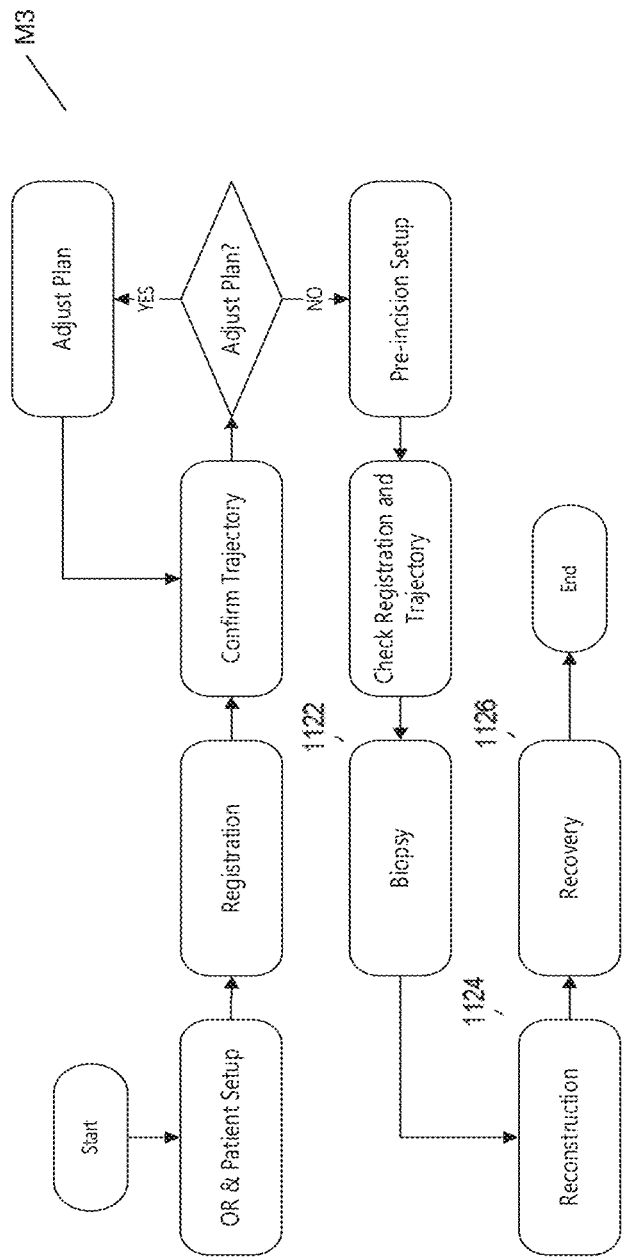
FIG. 11B is a flow diagram illustrating a method of performing a medical procedure, such as a frameless brain biopsy, by way of a navigation system, in accordance with an alternative embodiment of the present disclosure.

Still referring to FIG. 11A and ahead to FIG. 11B, for a brain biopsy, instead of resecting, the method M2 comprises inserting a thin needle into a patient's brain 102b, removing a sample of brain tissue using the thin needle, assessing the sample of brain tissue, e.g., by a pathologist (human and/or robotic characterizing equipment) to determine whether the sample of brain tissue is cancerous (malignant). For a brain biopsy, the method M2 optionally comprises using a stereotactic frame. While both types of procedures, e.g., resection and brain biopsy, are performed in the method M2 using image-guidance, the navigation system 200 is well-suited for handling frameless biopsies.

Referring to FIG. 11B, this flow diagram illustrates a method M3 of performing a medical procedure, such as a frameless brain biopsy, by way of a navigation system 200, in accordance with an alternative embodiment of the present disclosure. The brain biopsy surgical procedure is very similar to a port-based surgical procedure (FIG. 11A) with the exception that the method M3 comprises: performing a biopsy, as indicated by block 1122, reconstructing the surgical site, as indicated by block 1124, and recovering the patient 102, as indicated by block 1126, wherein such steps having different aspects. In the biopsy step (step 1122), a small hole is drilled into the skull at the engagement point.

Still referring to FIG. 11B, in the method M3, performing the biopsy, as indicated by block 1122, comprises guiding the biopsy needle through a hole, such as a cranial hole, into the brain 102b, and to the planned or relevant target tissue, tracking the biopsy needle in real-time, obtaining a biopsy sample, and disposing the biopsy sample in a container for transportation to a pathology laboratory. In the method M3, reconstructing the surgical site, as indicated by block 1124, and recovering the patient 102, as indicated by block 1126, have shorter durations than the corresponding steps in a resection for at least the reason that the cranial hole is much smaller. As noted above, the biopsy needle is also tracked continuously by the navigation system 200. In a further embodiment, the surgeon holds the biopsy needle, freehand, during the procedure. In other embodiments, in the method M3, performing the biopsy, as indicated by block 1122, further comprises adhering a needle guide, e.g., to the skull of the patient 102, positioning and orienting the needle guide using the navigation system 200. If the needle guide comprises a depth-stop, continuous navigation for the biopsy needle may be minimized or eliminated.

Figure 11C:
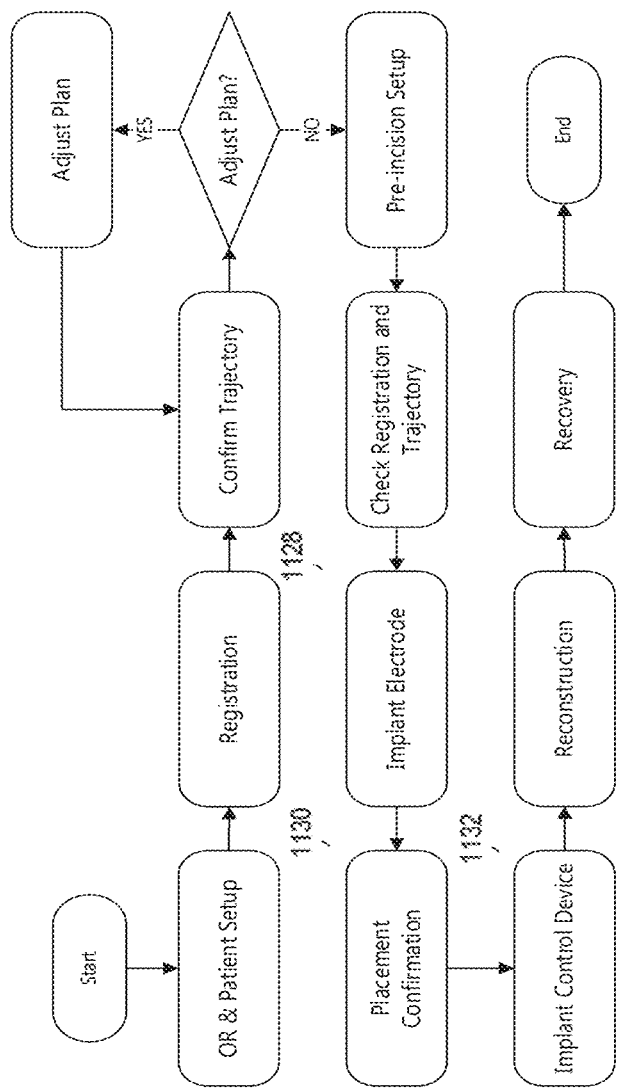
FIG. 11C is a flow diagram illustrating a method of performing a medical procedure, such as a frameless deep brain stimulation (DBS), by way of a navigation system, in accordance with an alternative embodiment of the present disclosure.

Referring to FIG. 11C, this flow diagram illustrates a method M4 of performing a medical procedure, such as a frameless DBS, by way of a navigation system 200, in accordance with an alternative embodiment of the present disclosure. In a DBS procedure, the method M4 comprises implanting an electrode, such as a small electrode, into a specific area of the brain 102b for reduction of tremors from Parkinson's disease and dystonia, wherein the electrode is connected to a control device implantable elsewhere in the body of the patient 102, typically near the clavicle. In the method M4, DBS is performable via a stereotactic frame or frameless technique; and the steps of the method M4 are similar to those of the method M3, as shown in FIG. 11C, and to the method M2, as shown in FIG. 11B, with the exception that the method M4 comprises: implanting an electrode, as indicated by block 1128, confirming placement, as indicated by block 1130, and implanting a control device, as indicated by block 1132.

Still referring to FIG. 11C, in the method M4, implanting an electrode, as indicated by block 1128, comprises forming a small hole, e.g., by drilling, in the skull at the engagement point, positioning and orienting a guidance device on the skull using the navigation system 200, guiding the electrode through the guidance device into the brain 102b to the planned target, e.g., the target tissue, and tracking the electrode in real-time using the navigation system 200. In the method M4, confirming placement, as indicated by block 1130, comprising at least one of: listening to activity on the electrode; and performing a test stimulation of an area of the brain 102b via the electrode and observing a patient response.

Still referring to FIG. 11C, in the method M4, implanting a control device, as indicated by block 1132, comprises: forming an incision at a location proximate a clavicle; subcutaneously inserting a control device; attaching the control device to the clavicle; subcutaneously routing at least one lead from the electrode leads to the control device. As in the method M2 (FIG. 11A), the method M4 comprises: reconstructing the surgical site, as indicated by block 1118; and recovering the patient 102, as indicated by block 1120.

Figure 11D:
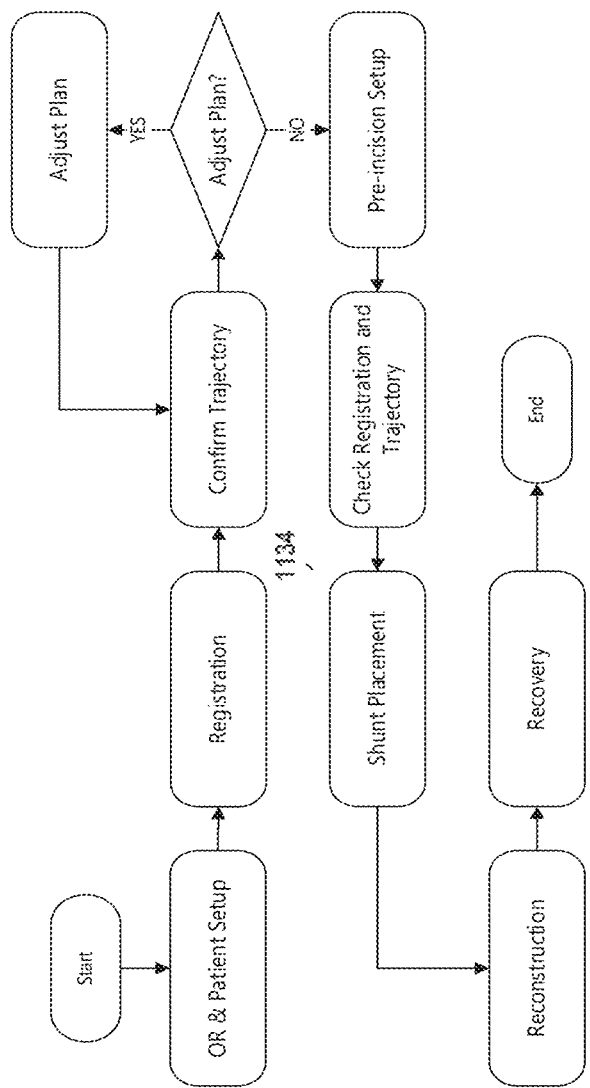
FIG. 11D is a flow diagram illustrating a method of performing a medical procedure, such as a catheter/shunt placement, by way of a navigation system, in accordance with an alternative embodiment of the present disclosure.

Referring to FIG. 11D, this flow diagram illustrates a method M5 of performing a medical procedure, such as a catheter/shunt placement, by way of a navigation system 200, in accordance with an alternative embodiment of the present disclosure. In general, catheter or shunt placement is assisted by the navigation system 200. Shunts or catheters are inserted into the brain cavity to treat patients with hydrocephalus. Cranial pressure is too great in these patients as a result of excessive cerebral spinal fluid (CSF). A shunt or catheter is introduced under image guidance of the navigation system 200; and the excess CSF is drained into another part of the body for reabsorption.

Still referring to FIG. 11D, a method M5 comprises steps that are similar to the method M3 (FIG. 11B) with the replacement of performing the biopsy, as indicated by block 1122, placing a shunt or catheter, as indicated by block 1134, wherein placing a shunt, as indicated by block 1134, comprises forming a small hole, e.g., by drilling, in the skull at the engagement point, positioning and orienting a guidance device on the skull using the navigation system 200, guiding the shunt or catheter through the guidance device into the brain 102b to the planned target, e.g., the target tissue, and tracking the shunt or catheter in real-time using the navigation system 200.

Referring back to FIGS. 1-11D, in an embodiment, during a surgical procedure, such as a port-base procedure, brain displacement or deformation can be predicted (modeled) with accurate simulation, using information, such as a priori tissue stiffness information, geometric information relating to the introducer and port, a biomechanical model of tissue deformation, (using the skull as a boundary condition) and using pre-operative imaging data. This model is updateable by using real-time imaging information as the introducer is positioned inside of the head, and more accurately, by real-time imaging being performed using data obtained via the in-situ port for obtaining and updating intra-operative data. For instance, real-time ultrasound imaging, being performed on the tip of the port, can detect tissue stiffness inside the brain. This information is useable instead of the a priori predicted stiffness and can provide a better estimate of tissue movement. In addition, ultrasound can be used to identify sulci patterns as the port is being introduced. These sulci patterns can be matched to the pre-operative sulcus patterns; and a deformed pre-operative model can be generated based on this information.

Referring back to FIGS. 1-11D, in this iterative manner, the model will be updated by the system according to information obtained during the procedure to provide for accurate representations of the tumor location, e.g., modeling of tumor roll within the brain and measurement of the total stress and strain on nerve fibers as the port is inserted into the brain. This information may be represented by the system as a global value; and, as with the weighting of the hierarchy of the fibers, the actual strain of the fibers may be used to calculate a value associated with the invasiveness of a surgical approach.

Referring back to FIGS. 1-11D, a discrepancy may exist among the pre-operative imaging data and the real-time port information (US, OCT, photo acoustic, optical). This discrepancy can be measured by matching sulci patterns, blood vessel positions, or by quantifiable common contrast mechanisms such as elastic modulus, tissue anisotropy, blood-flow, etc. The real-time port information is expected to represent accurate information; and, when a significant discrepancy is found, a scan is performed for updating the volumetric MRI and/or CT scans to update the pre-operative, or intra-operative, scanning volume. In the optimal configuration, an MRI port coil would be used in conjunction with an external MRI system to acquire a 3D volume demonstrating sulci path, tumor, nerve fascicles by way of diffusion tensor imaging (DTI) acquisition, and blood vessels. As the acquisition time is typically much longer than US, OCT or photo-acoustic imaging, a real-time modality is not expected to be used; however, it can be effectively utilized as a single modality to position the access port with pseudo-real time capability (typically not faster than 1 fps). Future availability of faster acquisition technologies may provide improved real-time DTI information using a port coil and is encompassed by the present disclosure.

Figure 12:
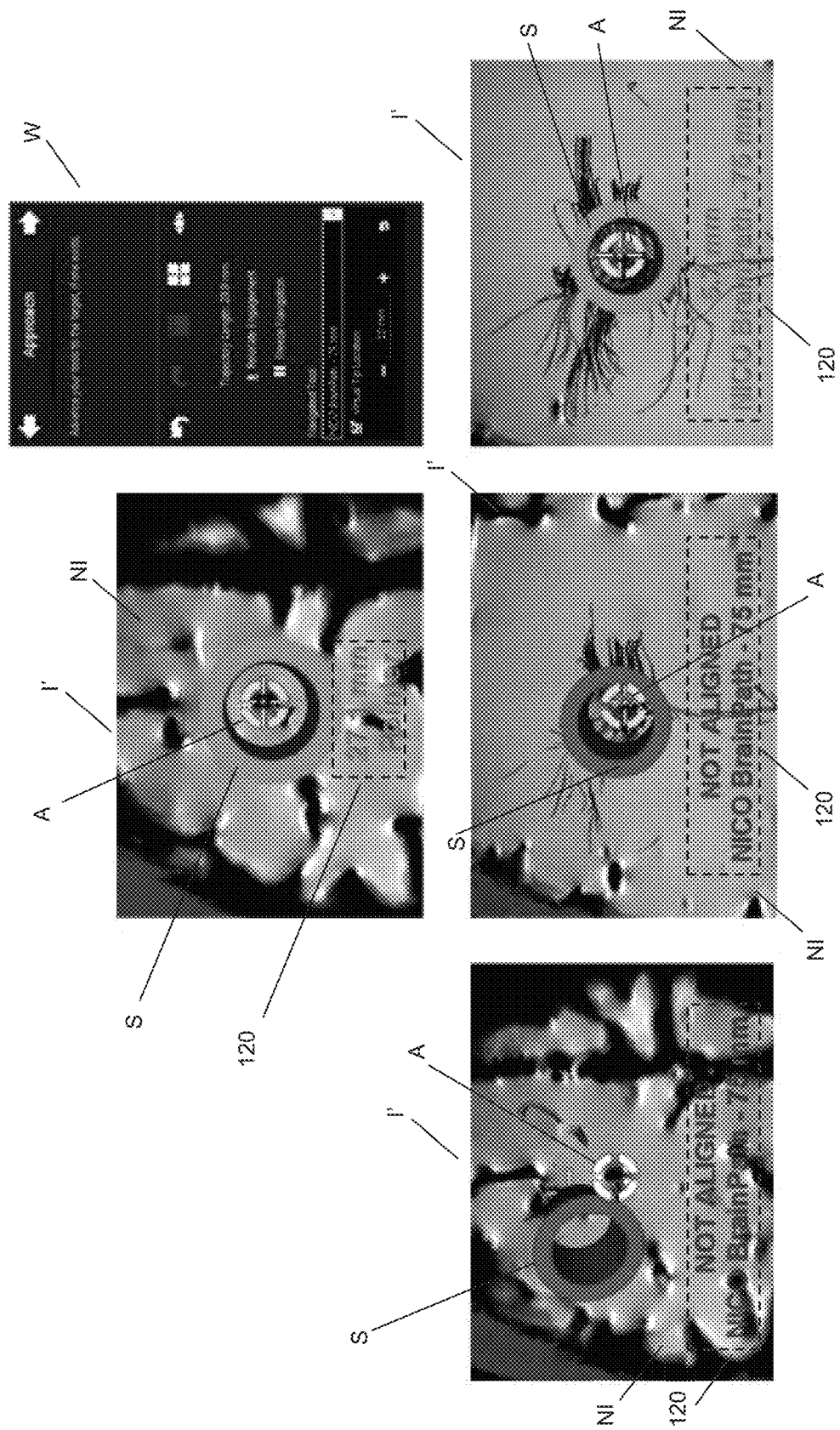
FIG. 12 is a screenshot illustrating various elements of a display renderable on at least one display device by way of using a navigation system, in accordance with an embodiment of the present disclosure.

Referring to FIG. 12, this diagram illustrates various elements of a display D renderable on at least one display device, such as the display devices 205, 211, by way of a navigation system 200 using an trajectory alignment system, in accordance with an embodiment of the present disclosure. The display D comprises at least one of an interactive navigation window W, at least one real-time navigation image I', a dashboard DB, and a sidebar SB (FIGS. 13 and 14). The interactive navigation window W displays information corresponding to a current stage, e.g., an "approach" stage, of a therapeutic procedure, such as a medical procedure and a surgical procedure, and comprises at least one feature for interactively confirming, revising, and updating trajectory information. The real-time navigation image I' comprises a real-time neural image NI and at least one indicia, such as textual navigation information 120, a navigation symbol S, e.g., a generally circular symbol, and an alignment symbol A, the alignment symbol A comprising a crosshair symbol CH and a generally circular boundary or a broken generally circular boundary CB, the crosshair symbol CH in movable relation to the generally circular boundary or a broken generally circular boundary CB.

Still referring to FIG. 12, the navigation symbol S is rendered at a location relative to the real-time neural image NI, the location of the navigation symbol S corresponding to at least one of a planned trajectory and an updated trajectory. The alignment symbol A is rendered at a location relative to the real-time neural image NI, the location of the alignment symbol A corresponding to real-time data corresponding to movement of a tracked or tracking tool (not shown), such as an access port, a pointer tool, a surgical tool, a stimulation tool, and the like. The navigation symbol S and the alignment symbol A are renderable as elements overlaying the real-time neural image NI, together, provide real-time feedback regarding alignment of the tracked tool in relation to a planned trajectory or an updated trajectory for facilitating neural navigation, whereby real-time alignment data is achievable, and whereby at least one neurological structure is preservable.

Still referring to FIG. 12, the navigation symbol S and the alignment symbol A, each comprise a color-coding feature for enhancing neural navigation. By example only, the navigation symbol S comprises a red color for indicating that the tracked tool is not aligned and a green color for indicating that the tracked tool is aligned. The generally circular boundary or a broken generally circular boundary CB of the alignment symbol A comprises a white "color" (or an absence of color) for indicating the tracked tool is outside a predetermined, or interactively set, proximity threshold in relation to the planned, or updated, trajectory and the crosshair symbol CH of the alignment symbol A comprises a yellow color for indicating that the tracked tool is near, or inside, a predetermined, or interactively set, proximity threshold in relation to the planned, or updated, trajectory. For example, when the system 200, using an trajectory alignment system, determines that the tracked tool is aligned within a predetermined, or interactively set, proximity threshold in relation to the planned, or updated, trajectory both the crosshair symbol CH and the generally circular boundary or a broken generally circular boundary CB (turns from white to yellow) of the alignment symbol A comprise a yellow color; and the navigation symbol S comprises a green color, wherein the alignment symbol A is disposed within the navigation symbol S.

Still referring to FIG. 12, by example only, the color green indicates that the tracked or tracking tool is on the planned trajectory; and the color yellow indicates that the tracked or tracking tool has reached the target, such the relevant target tissue, e.g., a tumour. If a surgeon is using a port tool or an access port, the sheath is advanced by the virtual tip distance for positioning an opening of the sheath at the location of the target. When the sheath has reached the target, the sheath is secured, such as by a "Shepherd's Hook;" and the obturator is removed. By example only, a red color indicates that the tracked tool is off the planned trajectory or is past the target.

Still referring to FIG. 12, by example only, the textual navigation information 120 comprises at least one of planned trajectory information, updated trajectory information, tracked tool identification information, and tracked tool location information, e.g., interactive data relating to a distance between a distal end of the tracked or tracking tool and a target, such as a target tissue. Further, such textual information is also renderable by the system 200, using a trajectory alignment system, on the at least one display device, such as the display devices 205, 211 via the interactive navigation window W. The window W also comprises interactive features, such as buttons for moving forward and backward in the therapeutic procedure, buttons for loading images and/or information from at least one database, and a dropdown menu for selecting a tool for tracking, by example only.

Still referring to FIG. 12, by using a pointer for aligning a tool to a trajectory, the alignment system facilitates alignment of an access port without the need for a tracked sheath, supports alignment of compatible miniframes, is available for use with a laptop computer, is configured to reconcile patient identification and name in a "merge" series, and facilitates changing a port length and to eliminate the need for port verification, in accordance with an alternative embodiment of the present disclosure. The alignment system facilitates performing an "approach" by using a pointer, provides a graphic feature whereby alignment becomes intuitive, and displays a trajectory length in the approach.

Figure 13A:
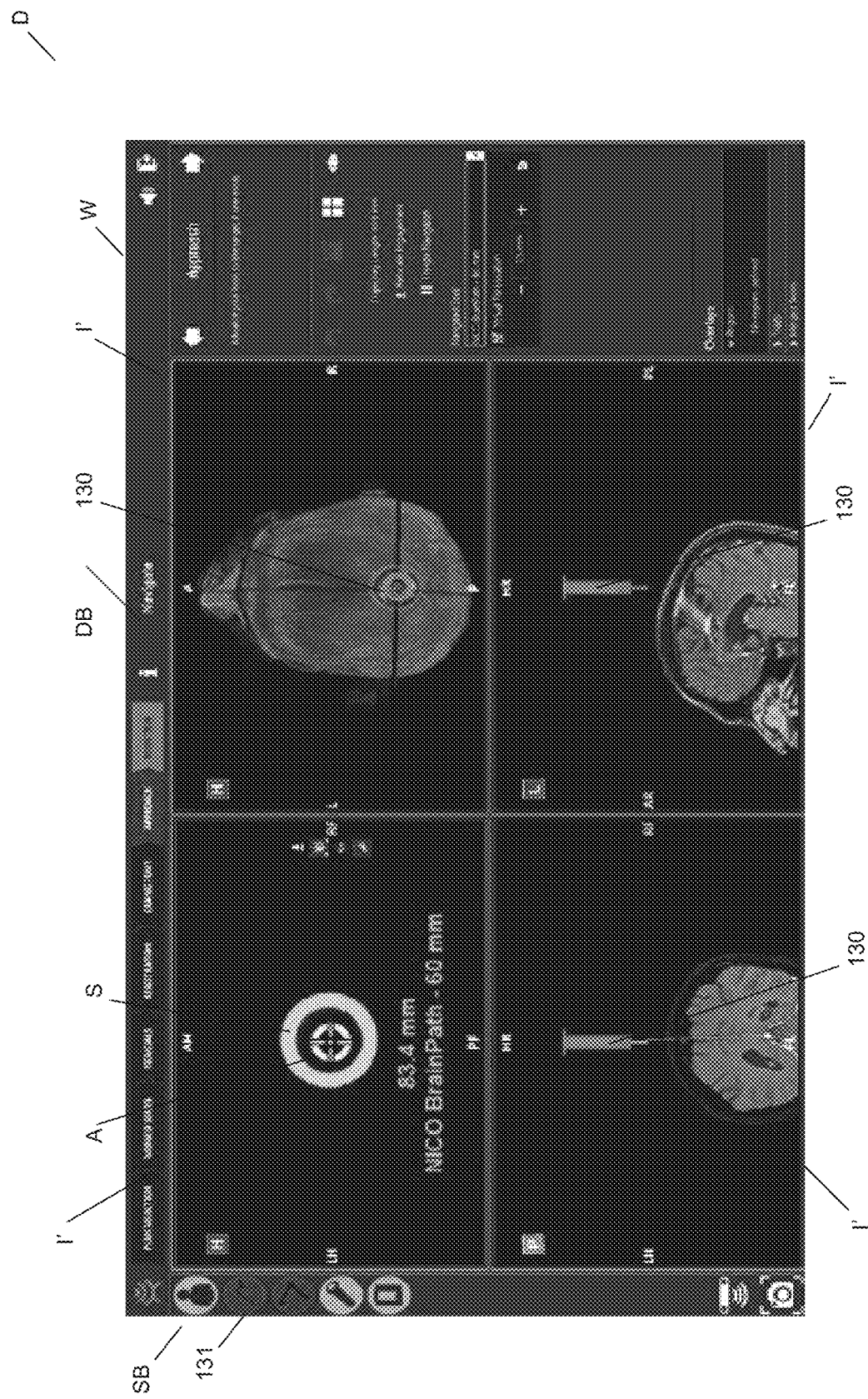
FIG. 13A is a further screenshot illustrating various elements of a display renderable on at least one display device by way of using a navigation system, in accordance with an embodiment of the present disclosure.
Figure 14:
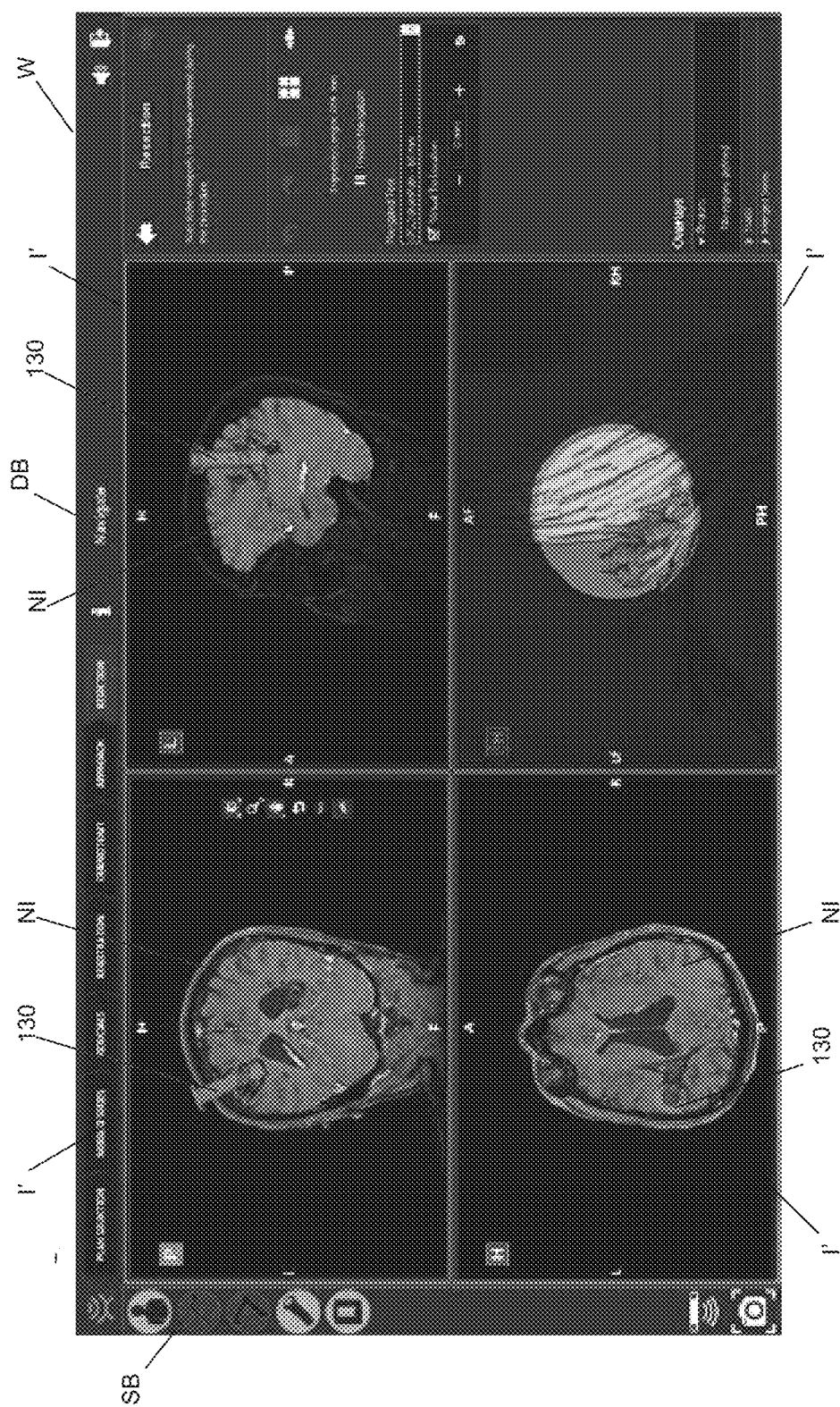
FIG. 14 is a screenshot illustrating a display renderable on at least one display device, by way of a navigation system using an trajectory alignment system, in accordance with an embodiment of the present disclosure.

Referring to FIG. 13A, this screenshot illustrates a display D renderable on at least one display device, such as the display devices 205, 211, by way of a navigation system 200 using an trajectory alignment system, in accordance with an embodiment of the present disclosure. The display D comprises at least one of an interactive navigation window W, at least one real-time navigation image I', a dashboard DB, and a sidebar SB. The interactive navigation window W displays information corresponding to a current stage, e.g., an "approach" stage, of a therapeutic procedure, such as a medical procedure and a surgical procedure, and comprises at least one feature for interactively confirming, revising, and updating trajectory information. The real-time navigation image I' comprises a real-time neural image NI and at least one indicia, such as textual navigation information 120, a navigation symbol S, e.g., a generally circular symbol, and an alignment symbol A, the alignment symbol A comprising a crosshair symbol CH and a generally circular boundary or a broken generally circular boundary CB, the crosshair symbol CH in movable relation to the generally circular boundary or a broken generally circular boundary CB.

Still referring to FIG. 13A, a system, such as the navigation system 200, for aligning a tool, such as the access port 206, in relation to a trajectory in real-time comprises: a processor, such as the processor 402, configurable by a set of executable instructions storable in relation to a non-transitory memory device. such as the memory 404, to: receive input data from at least one source, such as the devices 420, the tracking system 213, and the external devices 444, of at least one pre-operative plan image, at least one multi-modal image, and at least one real-time multi-modal image; interactively track at least one neural fiber, whereby interactively tracked fiber data is obtainable; automatically generate output data by way of data transformation using the input data and the interactively tracked neural fiber data; and transmit the output data to at least one of: at least one display device 205, 211, for rendering at least one real-time interactive navigation display D for facilitating neural navigation, and at least one drive device for positioning at least one tracking device in relation to the tool in real-time, whereby real-time alignment data is achievable, and whereby at least one neurological structure is preservable, in accordance with an embodiment of the present disclosure.

Still referring to FIG. 13A, the at least one indicia further comprises a tracked tool indicia 130, wherein the tracked tool indicia 130 comprise a color-coding feature for enhancing neural navigation. The color-coding feature comprises a blue color, by example only. Each real-time neural image NI comprises a distinct color coding feature, such as in the representation of bone or boney structures, wherein a distinct color is assignable for representing a particular cross-section of a patient's anatomy. In an "approach" stage of phase, the display D shows information about the trajectory created for this procedure, such as a planned trajectory, and the location of at least one tracked tool rendered as the tracked tool indicia 130. The window W, corresponding to an "approach" phase, is available if a planned trajectory exists for the given procedure. For example, a planned trajectory is creatable by using the BrightMatter® Plan or during the "targeting" phase.

Still referring to FIG. 13A, a method of fabricating a system, such as the system 200, for aligning a tool, such as an access port 206, in relation to a trajectory in real-time comprises: providing a processor, such as the processor 402, configurable by a set of executable instructions storable in relation to a non-transitory memory device. such as the memory 404, to: receive input data from at least one source, such as the devices 420, the tracking system 213, and the external devices 444, of at least one pre-operative plan image, at least one multi-modal image, and at least one real-time multi-modal image; interactively track at least one neural fiber, whereby interactively tracked fiber data is obtainable; automatically generate output data by way of data transformation using the input data and the interactively tracked neural fiber data; and transmit the output data to at least one display device, such as the display devices 205, 211, for rendering at least one real-time interactive navigation display D for facilitating neural navigation, whereby real-time alignment data is achievable, and whereby at least one neurological structure is preservable, in accordance with an embodiment of the present disclosure.

Figure 13B:
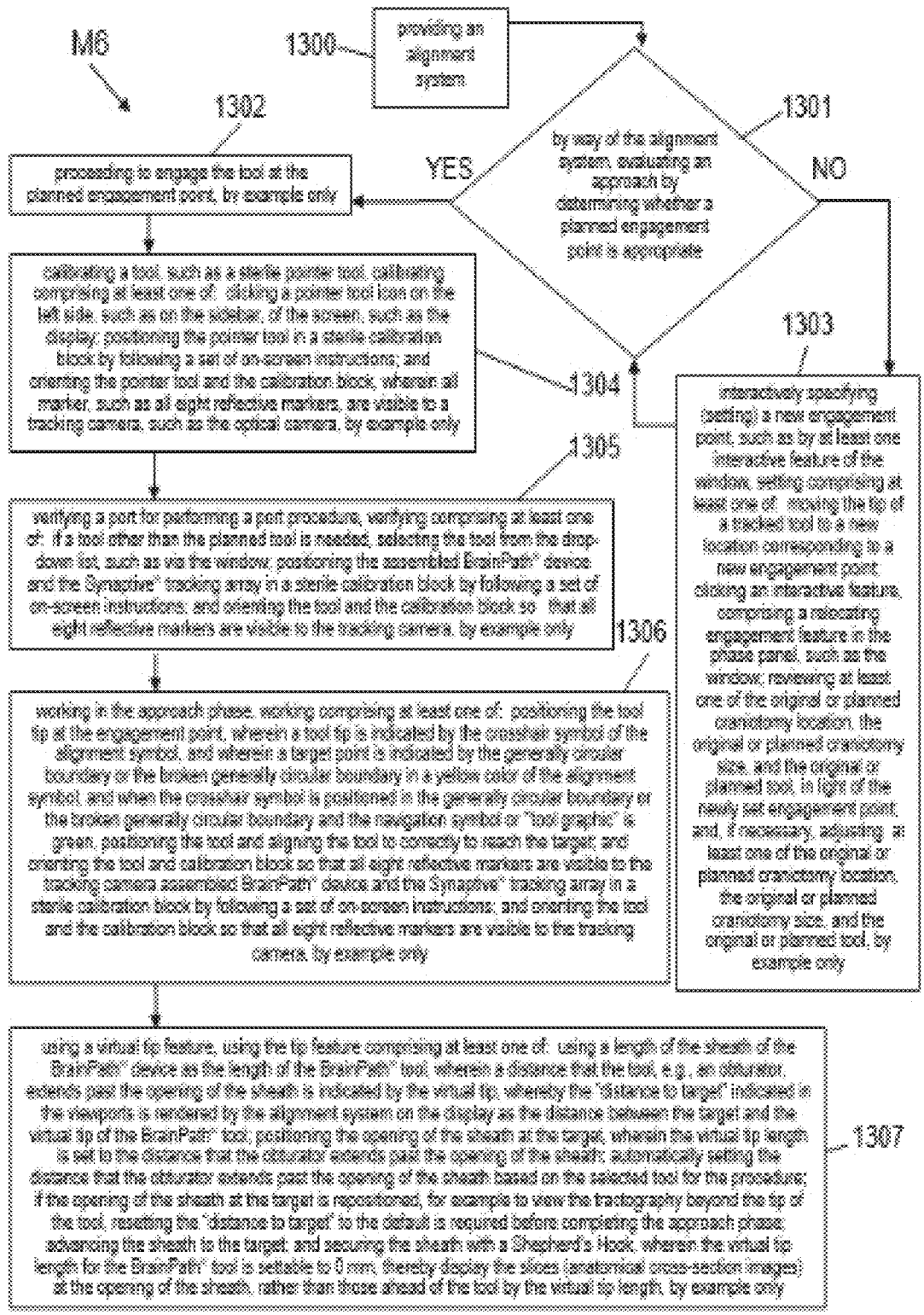
FIG. 13B is a flow diagram illustrates a method of aligning a tool in relation to a trajectory during an approach phase of a surgical procedure by way of an alignment system, in accordance with an embodiment of the present disclosure.

Referring to FIG. 13B, this flow diagram illustrates a method M6 of aligning a tool in relation to a trajectory during an approach phase of a surgical procedure by way of an alignment system, in accordance with an embodiment of the present disclosure. The method M6 comprises evaluating an approach by determining whether a planned engagement point is appropriate, as indicated by block 1301; if the planned engagement point is appropriate, proceeding to engage the tool at the planned engagement point, as indicated by block 1302; if the planned engagement point is not, or no longer, appropriate, e.g., by changed circumstances, interactively specifying a new engagement point, such as by at least one interactive feature of the window W, as indicated by block 1303; and returning to evaluating an approach by determining whether a planned engagement point is appropriate, as indicated by block 1301.

Still referring to FIG. 13B, a method of aligning a tool in relation to a trajectory in real-time by way of an alignment system comprises: providing the alignment system, as indicated by block 1300, the alignment system providing comprising providing a processor, such as the processor 402, configurable by a set of executable instructions storable in relation to a non-transitory memory device. such as the memory 404, to: receive input data from at least one source, such as the devices 420, the tracking system 213, and the external devices 444, of at least one pre-operative plan image, at least one multi-modal image, and at least one real-time multi-modal image; interactively track at least one neural fiber, whereby interactively tracked fiber data is obtainable; automatically generate output data by way of data transformation using the input data and the interactively tracked neural fiber data; and transmit the output data to at least one of: at least one display device 205, 211, for rendering at least one real-time interactive navigation display D for facilitating neural navigation, and at least one drive device for positioning at least one tracking device in relation to the tool in real-time, whereby real-time alignment data is achievable, and whereby at least one neurological structure is preservable; calibrating the tool by using a calibration block; if performing a port procedure, verifying a port; evaluating an approach by determining whether a planned engagement point is appropriate using the at least one real-time interactive navigation display of the alignment system; if the planned engagement point is appropriate, performing the approach; if the planned engagement point is inappropriate, interactively setting a new engagement point by way of at least one interactive feature of the alignment system; and optionally returning to the evaluating step, in accordance with another embodiment of the present disclosure.

Still referring to FIG. 13B, the method M6 further comprises calibrating a tool, such as a sterile pointer tool, as indicated by block 1304, wherein calibrating the pointer tool comprises: clicking a pointer tool icon 131 on the left side, such as on the sidebar SB, of the screen, such as the display D; positioning the pointer tool in a sterile calibration block by following a set of on-screen instructions; and orienting the pointer tool and the calibration block, wherein all marker, such as all eight reflective markers, are visible to a tracking camera, such as the optical camera 204.

Still referring to FIG. 13B, the method M6 further comprises verifying a port for performing a port procedure, as indicated by block 1305. Before using the system 200 to guide the approach for a port procedure, by example only, a Synaptive® tracking array is assembled in relation to the NICO® BrainPath® device and verified by using the calibration block. In the method M6, verifying the port comprises: (a) if a tool other than the planned tool is needed, selecting the tool from the drop-down list, such as via the window W; (b) positioning the assembled BrainPath® device and the Synaptive® tracking array in a sterile calibration block by following a set of on-screen instructions; and (c) orienting the tool and the calibration block so that all eight reflective markers are visible to the tracking camera. If a port tool verification attempt fails, the system 200, using a trajectory alignment system discards any previous port tool verifications. For example, if a 50 mm tool is verified, and a 60 mm tool has an attempted and failed verification, only the 50 mm tool is useable another tool is properly verified.

Still referring to FIG. 13B, the method M6 further comprises working in the approach phase, as indicated by block 1306, wherein working in the approach phase comprises: (a) positioning the tool tip at the engagement point, wherein a tool tip is indicated by the crosshair symbol CH of the alignment symbol A, and wherein a target point is indicated by the generally circular boundary or the broken generally circular boundary CB in a yellow color of the alignment symbol A; and (b) when the crosshair symbol CH is positioned in the generally circular boundary or the broken generally circular boundary CB and the navigation symbol S or "tool graphic" is green, positioning the tool and aligning the tool to correctly to reach the target; and (c) orienting the tool and calibration block so that all eight reflective markers are visible to the tracking camera. For example, if a 50 mm tool is verified and a 60 mm tool has an attempted and failed verification, only the 50 mm tool is useable another tool is properly verified at this stage as well. The viewport shows a target-centric view of the tool's distance from the target. By keeping the tool graphic concentric with the yellow broken circle, the tool stays on the planned trajectory, wherein a "distance to target" notification text in the viewport. This text changes color to indicate the status of the approach, wherein green indicates that the tool is on the planned trajectory, yellow indicates that the tool tip has reached the target, and red indicates that the Tool is off the planned trajectory or is past the target. If performing a port procedure, switching between tracking the BrainPath® device and the pointer tool is possible by selecting another tool from the drop-down list in the phase panel of the window W. If an open craniotomy procedure is being performed, only the pointer tool is available.

Still referring to FIG. 13B, in executing the method M6, the system 200 further uses a virtual tip feature in the approach phase, as indicated by block 1307, wherein the length of the sheath of the BrainPath® device is used as the length of the BrainPath® tool. The distance the obturator extends past the opening of the sheath is indicated by the virtual tip. In the approach phase, the "distance to target" indicated in the viewports is the distance between the target and the virtual tip of the BrainPath® tool. To position the opening of the sheath at the target, the virtual tip length must be set to the distance that the obturator extends past the opening of the sheath. The system 200, using a trajectory alignment system, automatically sets the distance that the obturator extends past the opening of the sheath based on the selected tool for the procedure. If the opening of the sheath at the target is repositioned, for example to view the tractography beyond the tip of the tool, resetting the "distance to target" to the default is required before completing the approach phase. When using the BrainPath® tool, once the sheath is advanced to the target and secured with the Shepherd's Hook, the virtual tip length for the BrainPath® tool is settable to 0 mm so that the viewports display the slices (anatomical cross-section images) at the opening of the sheath rather than those ahead of the tool by the virtual tip length.

Still referring to FIG. 13B, in the method M6, setting a new engagement point comprises: (a) moving the tip of a tracked tool to a new location corresponding to a new engagement point; (b) clicking an interactive feature, comprising a relocating engagement feature in the phase panel, such as the window W; (c) reviewing at least one of the original or planned craniotomy location, the original or planned craniotomy size, and the original or planned tool, in light of the newly set engagement point; and, (d) if necessary, adjusting at least one of the original or planned craniotomy location, the original or planned craniotomy size, and the original or planned tool.

Referring to FIG. 14, this screenshot illustrates a display D renderable on at least one display device, such as the display devices 205, 211, by way of a navigation system 200 using an trajectory alignment system, in accordance with an embodiment of the present disclosure. The display D comprises at least one of an interactive navigation window W, at least one real-time navigation image I', a dashboard DB, and a sidebar SB. The interactive navigation window W displays information corresponding to a current stage, e.g., a "resection" stage, of a therapeutic procedure, such as a medical procedure and a surgical procedure, and comprises at least one feature for interactively confirming, revising, and updating trajectory information. The real-time navigation image I' comprises a real-time neural image NI and at least one indicia, such as the tracked tool indicia 130. The viewports, such as the at least one real-time navigation image I', in the resection phase or stage facilitate orienting the anatomy to the at least one plan image. One viewport shows the plan images from the perspective of the BrainPath® sheath at its current position. The other viewports show orthogonal views of the plan images. When the pointer tool is in the tracking camera's field of view, its image appears in the viewports. The virtual tip length in the resection phase is set to 0 mm by default in this phase. To show the tractography ahead of the tool in the viewports, clicking the up arrow increases the virtual tip length by a desired amount.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, are also encompassed by the present disclosure.

INDUSTRIAL APPLICABILITY

The subject matter of the present disclosure industrially applies to the field of image guided medical procedures. More particularly, subject matter of the present disclosure industrially applies to the field of patient reference tools for rapid registration in relation to image guided medical procedures. Even more particularly, subject matter of the present disclosure industrially applies to the field of assisting patient reference tools for rapid registration in relation to image guided medical procedures.

The invention claimed is:

1. A system for aligning a tool in relation to a trajectory and sulci locations of a brain in real-time, the system comprising:
  a user interface, the user interface comprising at least one display device for rendering at least one real-time interactive navigation display for facilitating neural navigation, the at least one real-time interactive navigation display comprising an interactive navigation window and at least one real-time navigation image, the interactive navigation window displaying information corresponding to a current stage of a therapeutic procedure, and the at least one real-time navigation image comprising a real-time neural image, indicia, a navigation symbol, and an alignment symbol, the indicia comprising textual navigation information, the textual navigation information comprising planned trajectory information, updated trajectory information, tracked tool identification information, and tracked tool location information, and the textual navigation information rendered via the interactive navigation window, a location of the navigation symbol corresponding to one of a planned trajectory and an updated trajectory, a location of the alignment symbol corresponding to real-time data relating to movement of the tool, the tool comprising one of a tracked tool and a tracking tool, the tracked tool location information comprising data relating to a distance between a distal end of the tracked tool and a target, and the navigation symbol and the alignment symbol overlaying the real-time neural image, whereby real-time feedback regarding alignment of the tool in relation to one of a planned trajectory and an updated trajectory for facilitating neural navigation is provided;
  at least one drive device for positioning at least one tracking device in relation to the tool in real-time; and
  a processor configured to:
    receive input data from a plurality of sources, the input data comprising a plurality of images corresponding to the plurality of sources, the plurality of images comprising at least one of: a plurality of real-time multi-modal images corresponding to a plurality of imaging modalities, at least one pre-operative plan image, and at least one pre-operative multi-modal image;
    interactively track at least one neural fiber, whereby interactively tracked fiber data is obtainable;
    measure at least one absolute quantitative metric, the at least one absolute quantitative metric comprising tissue stiffness;
    update a priori predicted tissue stiffness in a biomechanical model of the brain using detected tissue stiffness information based on the plurality of real-time multi-modal images, whereby sulci patterns are identified in real time;
    correct the trajectory in relation to the sulci locations based on the sulci patterns identified in real time;
    quantitatively register the plurality of images using the absolute quantitative metric to register the plurality of images for providing transformed real-time data to a user interface, the transformed real-time data comprising real-time registration data in relation to real-time neural network data, the real-time neural network data comprising the interactively tracked fiber data, real-time data relating to the sulci locations, and real-time data relating to the sulci patterns;
    update registration data by one of manipulating and transforming the registration data to ensure a best match for a surgical area of interest while ignoring non-uniform tissue deformation affecting an area outside the surgical area of interest;
    automatically generate output data by way of data transformation using the input data and the real-time neural network data comprising: the interactively tracked neural fiber data the real-time data relating to the sulci locations, and the real-time data relating to the sulci patterns; and
    transmit the output data to the at least one display device and the at least one drive device,
  wherein the alignment symbol comprises a crosshair symbol and at least one of a circular boundary and a broken circular boundary, the crosshair symbol movable in relation to at least one of the circular boundary and the broken circular boundary,
  wherein the navigation symbol comprises a red color for indicating an absence of alignment of the tracked tool and a green color for indicating alignment of the tracked tool,
  wherein at least one of the circular boundary and the broken circular boundary comprises a white color for indicating that the tracked tool is outside at least one of: a predetermined proximity threshold in relation to the planned trajectory and an interactively set proximity threshold in relation to the updated trajectory,
  wherein the crosshair symbol comprises a yellow color for indicating that the tracked tool is disposed in relation to at least one of: near the predetermined proximity threshold, within the predetermined proximity threshold, near the interactively set proximity threshold, within the interactively set proximity threshold, and at the target,
  wherein the indicia further comprises a tracked tool indicia,
  wherein the tracked tool indicia comprises a color-coding feature for enhancing neural navigation, and
  wherein the at least one real-time navigation image comprises a plurality of real-time navigation images corresponding to a plurality of viewports, the plurality of viewports corresponding to orthogonal views of a plurality of plan images,
  wherein the processor is further configured to:
  if performing a port procedure, verify a port;
  evaluate an approach by determining whether a planned engagement point is appropriate using the at least one real-time interactive navigation display of the alignment system;
  if the planned engagement point is appropriate, instruct performing the approach by:

instructing displaying a target-centric view of a distance between the tool tip and a target;

instructing concentrically maintaining the tool symbol within at least one of a circular boundary and a broken circular boundary in a yellow color of the alignment symbol, thereby aligning and maintaining the tool on at least one of the planned trajectory and the updated trajectory, and whereby a notification text regarding the distance between the tool tip and the target is renderable via the at least one real-time interactive navigation display, the notification text comprising a color-coding feature for indicating a status of the approach, wherein the green color indicates that the tool is on at least one of the planned trajectory and the updated trajectory, wherein the yellow color indicates that the tool tip has reached the target, and wherein a red color indicates that the tool is one of: off the planned trajectory, off the updated trajectory, and past the target; and if another tool is needed, instructing displaying a dropdown menu of the at least one real-time interactive navigation display from which the other tool is selectable;

instructing using the virtual tip feature, a length of a sheath useable as a length of the tool, a distance that an obturator extends beyond a distal opening of the sheath indicable by the virtual tip, a distance between the tool tip and the target comprising a distance between the virtual tip and the target;

instructing positioning the distal opening of the sheath at the target by setting the virtual tip length to the distance that the obturator extends beyond the distal opening of the sheath;

automatically set the distance that the obturator extends beyond the distal opening of the sheath based on the selected tool for the procedure;

if the distal opening of the sheath is repositioned at the target, reset a distance-to-target value to a default value; and if the distal opening of the sheath reaches the target, instructing securing the sheath and setting the virtual tip length to 0 mm, whereby the at least one neural image displays at least one cross-section of anatomy proximate the distal opening of the sheath; and if the planned engagement point is inappropriate, interactively set a new engagement point by way of at least one interactive feature of the alignment system and evaluating a new approach, whereby at least one of: at least one axonal connection, the at least one neural fiber, and at least one neural pathway is preservable, whereby damage to brain circuitry is preventable, and whereby at least one image of a neurological structure is preservable.

2. The system of claim 1,
wherein the at least one real-time interactive navigation display further comprises at least one of at least one real-time navigation image, and a dashboard, and a sidebar, and
wherein the at least one drive device comprises at least one arm.

3. The system of claim 2,
wherein the therapeutic procedure comprises one of a medical procedure and a surgical procedure,
wherein the interactive navigation window comprises at least one feature for interactively confirming, revising, and updating trajectory information,
wherein the interactive navigation window comprises at least one interactive feature of at least one button for moving through at least one phase of a therapeutic procedure, at least one button for loading at least one of images and information from at least one database, and a dropdown menu for selecting a tool for tracking, and
wherein the at least one arm comprises at least one robotic arm.

4. The system of claim 3, wherein the at least one tracking device comprises at least one of an optical camera, a radio-frequency tracking device, and an electromagnetic tracking device.

5. The system of claim 4, wherein the target comprises a target tissue, and wherein the tracking tool comprises a pointer tool.

6. The system of claim 4, wherein the tracked tool comprises at least one of an access port, a surgical tool, and a stimulation tool.

7. The system of claim 5, wherein the navigation symbol and the alignment symbol, each comprise a color-coding feature for enhancing neural navigation.

8. The system of claim 4, wherein the color-coding feature of the tracked tool indicia comprises a blue color.

9. The system of claim 4, wherein the at least one real-time neural image comprises a distinct color coding feature for representing tissue comprising bone, and wherein the distinct color is assignable for representing a particular cross-section of a patient's anatomy.

10. The system of claim 1,
wherein the interactive navigation window is displayed if a planned trajectory exists for the therapeutic procedure, and
wherein a planned trajectory is creatable by during a targeting phase of the therapeutic procedure.

* * * * *